US010301384B2

(12) United States Patent
Vicari et al.

(10) Patent No.: US 10,301,384 B2
(45) Date of Patent: May 28, 2019

(54) ANTIBODIES TO IL-15

(71) Applicant: CALYPSO BIOTECH SA, Plan-les-Ouates (FR)

(72) Inventors: Alain Vicari, Neydens (FR); Olivier Leger, Saint-Sixt (FR)

(73) Assignee: CALYPSO BIOTECH SA, Plan-les-Ouates (CH)

(*) Notice: Subject to any disclaimer, the term of this patent is extended or adjusted under 35 U.S.C. 154(b) by 54 days.

(21) Appl. No.: 15/320,763

(22) PCT Filed: Jul. 1, 2015

(86) PCT No.: PCT/EP2015/064931
§ 371 (c)(1),
(2) Date: Dec. 21, 2016

(87) PCT Pub. No.: WO2016/001275
PCT Pub. Date: Jan. 7, 2016

(65) Prior Publication Data
US 2017/0137511 A1  May 18, 2017

(30) Foreign Application Priority Data

Jul. 2, 2014 (EP) .................................. 14175361

(51) Int. Cl.
*C07K 16/24* (2006.01)
*A61K 39/395* (2006.01)
*G01N 33/53* (2006.01)
*G01N 33/68* (2006.01)
*A61K 39/00* (2006.01)

(52) U.S. Cl.
CPC ....... *C07K 16/244* (2013.01); *G01N 33/6869* (2013.01); *A61K 2039/505* (2013.01); *C07K 2317/24* (2013.01); *C07K 2317/33* (2013.01); *C07K 2317/34* (2013.01); *C07K 2317/56* (2013.01); *C07K 2317/76* (2013.01); *C07K 2317/92* (2013.01); *G01N 2333/5443* (2013.01); *G01N 2333/7155* (2013.01)

(58) Field of Classification Search
CPC ............ C07K 16/244; A61K 2039/505; G01N 2333/5443
See application file for complete search history.

(56) References Cited

FOREIGN PATENT DOCUMENTS

WO   WO 03/017935    3/2003
WO   WO 2004/076620  9/2004

OTHER PUBLICATIONS

Vicari, A. P. et al. "Discovery and characterization of a novel humanized anti-IL-15 antibody and its relevance for the treatment of refractory celiac disease and eosinophilic esophagitis" *MABS*, 2017, pp. 1-19.
Zanoni, I. et al. "IL-15 cis Presentation Is Required for Optimal NK Cell Activation in Lipopolysaccharide-Mediated Inflammatory Conditions" *Cell Reports*, Sep. 23, 2016, pp. 1235-1249, vol. 4.
Baslund, B. et al. "Targeting Interleukin-15 in Patients With Rheumatoid Arthritis" *Arthritis & Rheumatism*, Sep. 2005, pp. 2686-2692, vol. 52, No. 9.
Bergamaschi, C. et al. "Circulating IL-15 exists as heterodimeric complex with soluble IL-15Rα in human and mouse serum" *Blood*, Jul. 5, 2012, pp. e1-e8, vol. 120, No. 1.
Bernard, J. et al. "Identification of an Interleukin-15α Receptor-binding Site on Human Interleukin-15" *The Journal of Biological Chemistry*, Jun. 4, 2004, pp. 24313-24322, vol. 279, No. 29.
Cario, G. et al. "High Interleukin-15 Expression Characterizes Childhood Acute Lymphoblastic Leukemia With Involvement of the CNS" *Journal of Clinical Oncology*, Oct. 20, 2007, pp. 4813-4820, vol. 25, No. 30.
Edelman, G. M. et al. "The Covalent Structure of an Entire $_\gamma$G Immunoglobulin Molecule" *Biochemistry*, Mar. 21, 1969, pp. 78-85, vol. 63, No. 1.
Fehniger, T. A. et al. "Interleukin 15: biology and relevance to human disease" *Blood*, Jan. 1, 2001, pp. 14-32, vol. 97, No. 1.
Ferrari-Lacraz, S. et al. "An Antagonist IL-15/Fc Protein Prevents Costimulation Blockade-Resistant Rejection" *Journal of Immunology*, Sep. 15, 2001, pp. 3478-3485, vol. 167, No. 6.
Finch, D. K. et al. "Identification of a potent anti-IL-15 antibody with opposing mechanisms of action in vitro and in vivo" *British Journal of Pharmacology*, 2011, pp. 480-490, vol. 162, No. 2.
Fulmer, T. et al. "Intercepting IL-15 in celiac disease" *SciBX*, Sep. 17, 2009, pp. 1-4, vol. 2, No. 36.
Holliger, P. et al. "Engineered antibody fragments and the rise of single domains" *Nature Biotechnology*, Sep. 2005, pp. 1126-1136, vol. 23, No. 9.
Jiang, B. et al. "Salvianolic acid B functioned as a competitive inhibitor of matrix metalloproteinase-9 and efficiently prevented cardiac remodeling" *BMC Pharmacology*, 2010, pp. 1-10, vol. 10, No. 10.
Kellog, B. A. et al. "Disulfide-Linked Antibody—Maytansinoid Conjugates: Optimization of In Vivo Activity by Varying the Steric Hindrance at Carbon Atoms Adjacent to the Disulfide Linkage" *Bioconjugate Chemistry*, Mar. 22, 2011, pp. 717-727, vol. 22.
Lebrec, H. et al. "Homeostasis of Human NK Cells Is Not IL-15 Dependent" *The Journal of Immunology*, Nov. 2013, pp. 5551-5558, vol. 191, No. 11.
Litinskiy, M. B. et al. "DCs induce CD40-independent immunoglobulin class switching through BLyS and APRIL" *Nature Immunology*, Sep. 2002, pp. 822-829, vol. 3, No. 9.
Lowe, D. C. et al. "Engineering a High-Affinity Anti-IL-15 Antibody: Crystal Structure Reveals an α-Helix in VH CDR3 as Key Component of Paratope" *Journal of Molecular Biology*, 2011, pp. 160-175, vol. 406.
Malamut, G. et al. "IL-15 triggers an antiapoptotic pathway in human intraepithelial lymphocytes that is a potential new target in celiac disease-associated inflammation and lymphomagenesis" *The Journal of Clinical Investigation*, Jun. 2010, pp. 2131-2143, vol. 120, No. 6.

(Continued)

*Primary Examiner* — Prema M Mertz
(74) *Attorney, Agent, or Firm* — Saliwanchik, Lloyd & Eisenschenk

(57) ABSTRACT

The present invention relates to antibodies binding IL-15, in particular humanized antibodies. In particular, the anti-IL-15 antibodies according to the invention are able to neutralize IL-15 activity and are useful in the prevention and/or treatment of an autoimmune disease and/or inflammatory disorder, a malignancy, transplant rejection, metabolic condition and/or an infectious disease caused by parasitic, viral or bacterial pathogens.

11 Claims, 5 Drawing Sheets

Specification includes a Sequence Listing.

(56) References Cited

OTHER PUBLICATIONS

Martinez-Hernandez, P. L. et al. "Serum interleukin-15 levels in cancer patients with cachexia" *Oncology Reports*, 2012, pp. 1443-1452, vol. 28, No. 4.

Nanayakkara, M. et al. "An undigested gliadin peptide activates innate immunity and proliferative signaling in enterocytes: the role in celiac disease" *The American Journal of Clinical Nutrition*, 2013, pp. 1123-1135, vol. 98.

Ohta, N. et al. "IL-15 Dependent Activation-Induced Cell Death-Resistant Th1 Type CD8 $\alpha\beta^+$NK1.1$^+$ T Cells for the Development of Small Intestinal Inflammation" *The Journal of Immunology*, 2002, pp. 460-468, vol. 169, No. 1.

Raschke, S. et al. "Adipo-Myokines: Two Sides of the Same Coin—Mediators of Inflammation and Mediators of Exercise" *Mediators of Inflammation*, 2013, pp. 1-16, vol. 2013, Article ID 320724.

Ratthé, C. et al. "Interleukin-15 enhances human neutrophil phagocytosis by a Syk-dependent mechanism: importance of the IL-15R$\alpha$ chain" *Journal of Leukocyte Biology*, Jul. 2004, pp. 162-168, vol. 76, No. 1.

Rentzos, M. et al. "IL-15 Is Elevated in Cerebrospinal Fluid of Patients With Alzheimer's Disease and Frontotemporal Dementia" *Journal of Geriatric Psychiatry and Neurology*, 2006, pp. 114-117, vol. 19, No. 2.

Stonier, S. W. et al. "Trans-presentation: A novel mechanism regulating IL-15 delivery and responses" *Immunology Letters*, 2010, pp. 85-92, vol. 127, No. 2.

Timmerman, P. et al. "Functional reconstruction and synthetic mimicry of a conformational epitope using CLIPS™ technology" *Journal of Molecular Recognition*, 2007, pp. 283-299, vol. 20.

Villadsen, L. S. "Resolution of psoriasis upon blockade of IL-15 biological activity in a xenograft mouse model" *The Journal of Clinical Investigation*, Nov. 2003, pp. 1571-1580, vol. 112, No. 10.

Zhu, X. et al. "Interleukin-15 expression is increased in human eosinophilic esophagitis and mediates pathogenesis in mice" *Gastroenterology*, Jul. 2010, pp. 182-193, vol. 139, No. 1.

Written Opinion in International Application No. PCT/EP2015/064931, dated Nov. 3, 2015, pp. 1-8.

Committee for Orphan Medicinal Products, "Public summary of opinion on orphan designation—Humanised monoclonal antibody targeting interleukin-15 for the treatment of eosinophilic oesophagitis" *European Medicines Agency*, Jul. 4, 2016, pp. 1-5.

(A)

```
cVH2  EVRLLASGGGLVKPGGSLKLSCAASEFTFSNYAMSWVRQTPEKRLEWVATISRGGDYTYY  60
cVH3  EVQLLASGGGLVKPGGSLKLSCAASEFTFSNYAMSWVRQTPEKRLEWVATISRGGDYTYY  60
cVH1  EVRLMASGGGLVKPGGSLKLSCAASEFTFSNYAMSWVRQTPEKRLEWVATISRGGDYTYY  60
cVH4  EVRLMESGGGLVKPGGSLKLSCAASEFTFSNYAMSWVRQTPEKRLEWVATISRGGDYTYY  60
hVH1  EVRLMASGGGLVQPGGSLRLSCAASEFTFSNYAMSWVRQAPGKGLEWVATISRGGDYTYY  60
                              *                    **         * cVH2  PDSVKGRFTISRDNAKNTLYLQMSSLRSEDTALYYCARRVSMITGGWAMDYWGQGTSVTV  120
cVH3  PDSVKGRFTISRDNAKNTLYLQMSSLRSEDTALYYCARRVSMITGGWAMDYWGQGTSVTV  120
cVH1  PDSVKGRFTISRDNAKNTLYLQMSSLRSEDTALYYCARRVSMITGGWAMDYWGQGTSVTV  120
cVH4  PDSVKGRFTISRDNAKNTLYLQMSSLRSEDTALYYCARRVSMITGGWAMDYWGQGTSVTV  120
hVH1  PDSVKGRFTISRDNSKNTLYLQMNSLRAEDTAVYYCARRVSMITGGWAMDYWGQGTLVTV  120
                    *         *     **  *                      * cVH2  SS  122
cVH3  SS  122
cVH1  SS  122
cVH4  SS  122
hVH1  SS  122
```

(B)

```
cVK1  DVLMTQTPLSLPVSLGDQASISCRSSQSIVDITGNTYLEWYLQKPGQSPKLLIYKVENRE  60
hVK1  DVVMTQSPLSLPVTLGQPASISCRSSQSIVDITGNTYLEWYQQRPGQSPRLLIYKVENRE  60
hVK2  EVVMTQSPATLSLSPGERATLSCRSSQSIVDITGNTYLEWYQQKPGQAPRLLIYKVENRE  60
         *  *    *  *    *  *                     *    *  * cVK1  SGVPDRESGSGSGTDFTLKISRVEAEDLGLYYCFQDSFVPYTFGQGTKLEIK  112
hVK1  SGVPDRFSGSGSGTDFTLKISRVEAEDVGVYYCFQDSFVPYTFGQGTKLEIK  112
hVK2  SGIPARFSGSGSGTDFTLTISSLEPEDFAVYYCFQDSFVPYTFGQGTKLEIK  112
        *  *             *  *   * *  *
```

Figure 1

SEQUENCE LISTING

<160> NUMBER OF SEQ ID NOS: 43

<210> SEQ ID NO 1
<211> LENGTH: 114
<212> TYPE: PRT
<213> ORGANISM: Homo sapiens

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 2
<211> LENGTH: 114
<212> TYPE: PRT
<213> ORGANISM: Mus musculus

<400> SEQUENCE: 2

Asn Trp Ile Asp Val Arg Tyr Asp Leu Glu Lys Ile Glu Ser Leu Ile
1               5                   10                  15

Gln Ser Ile His Ile Asp Thr Thr Leu Tyr Thr Asp Ser Asp Phe His
            20                  25                  30

Pro Ser Cys Lys Val Thr Ala Met Asn Cys Phe Leu Leu Glu Leu Gln
        35                  40                  45

Val Ile Leu His Glu Tyr Ser Asn Met Thr Leu Asn Glu Thr Val Arg
50                  55                  60

Asn Val Leu Tyr Leu Ala Asn Ser Thr Leu Ser Ser Asn Lys Asn Val
65                  70                  75                  80

Ala Glu Ser Gly Cys Lys Glu Cys Glu Glu Leu Glu Glu Lys Thr Phe
                85                  90                  95

Thr Glu Phe Leu Gln Ser Phe Ile Arg Ile Val Gln Met Phe Ile Asn
            100                 105                 110

Thr Ser

<210> SEQ ID NO 3
<211> LENGTH: 114
<212> TYPE: PRT
<213> ORGANISM: rat

<400> SEQUENCE: 3

Asn Trp Ile Asp Val Arg Tyr Asp Leu Glu Lys Ile Glu Ser Leu Ile
1               5                   10                  15

Gln Phe Ile His Ile Asp Thr Thr Leu Tyr Thr Asp Ser Asp Phe His
            20                  25                  30

Pro Ser Cys Lys Val Thr Ala Met Asn Cys Phe Leu Leu Glu Leu Gln
        35                  40                  45

Val Ile Leu His Glu Tyr Ser Asn Met Thr Leu Asn Glu Thr Val Arg
50                  55                  60

Asn Val Leu Tyr Leu Ala Asn Ser Thr Leu Ser Ser Asn Lys Asn Val
65                  70                  75                  80

```
Ile Glu Ser Gly Cys Lys Glu Cys Glu Glu Leu Glu Glu Arg Asn Phe
                85                  90                  95

Thr Glu Phe Leu Gln Ser Phe Ile His Ile Val Gln Met Phe Ile Asn
            100                 105                 110

Thr Ser

<210> SEQ ID NO 4
<211> LENGTH: 114
<212> TYPE: PRT
<213> ORGANISM: Rhesus macaque / Cynomolgus monkey

<400> SEQUENCE: 4

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser His Glu Ser Gly Asp Thr Asp Ile His Asp Thr Val Glu
        50                  55                  60

Asn Leu Ile Ile Leu Ala Asn Asn Ile Leu Ser Ser Asn Gly Asn Ile
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 5
<211> LENGTH: 122
<212> TYPE: PRT
<213> ORGANISM: Artificial Sequence
<220> FEATURE:
<223> OTHER INFORMATION: huVH1

<400> SEQUENCE: 5

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
                20                  25                  30

Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Trp Ala Met Asp Tyr Trp
            100                 105                 110

Gly Gln Gly Thr Leu Val Thr Val Ser Ser
            115                 120

<210> SEQ ID NO 6
<211> LENGTH: 122
<212> TYPE: PRT
<213> ORGANISM: Artificial Sequence
```

```
<220> FEATURE:
<223> OTHER INFORMATION: huVH2

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Arg Gly Gly Asp Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Trp Ala Met Asp Tyr Trp
            100                 105                 110

Gly Gln Gly Thr Leu Val Thr Val Ser Ser
        115                 120

<210> SEQ ID NO 7
<211> LENGTH: 122
<212> TYPE: PRT
<213> ORGANISM: Artificial Sequence
<220> FEATURE:
<223> OTHER INFORMATION: huVH3

<400> SEQUENCE: 7

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Arg Gly Gly Asp Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Trp Ala Met Asp Tyr Trp
            100                 105                 110

Gly Gln Gly Thr Leu Val Thr Val Ser Ser
        115                 120

<210> SEQ ID NO 8
<211> LENGTH: 122
<212> TYPE: PRT
<213> ORGANISM: Artificial Sequence
<220> FEATURE:
<223> OTHER INFORMATION: huVH4

<400> SEQUENCE: 8

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30
```

```
Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Leu Ile Thr Gly Gly Trp Ala Met Asp Tyr Trp
                100                 105                 110

Gly Gln Gly Thr Leu Val Thr Val Ser Ser
            115                 120
```

<210> SEQ ID NO 9
<211> LENGTH: 122
<212> TYPE: PRT
<213> ORGANISM: Artificial Sequence
<220> FEATURE:
<223> OTHER INFORMATION: huVH5

<400> SEQUENCE: 9

```
Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Glu Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Phe Ile Thr Gly Gly Trp Ala Met Asp Tyr Trp
                100                 105                 110

Gly Gln Gly Thr Leu Val Thr Val Ser Ser
            115                 120
```

<210> SEQ ID NO 10
<211> LENGTH: 122
<212> TYPE: PRT
<213> ORGANISM: Artificial Sequence
<220> FEATURE:
<223> OTHER INFORMATION: huVH6

<400> SEQUENCE: 10

```
Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Arg Val Ser Ile Ile Thr Gly Gly Trp Ala Met Asp Tyr Trp
            100                 105                 110

Gly Gln Gly Thr Leu Val Thr Val Ser Ser
        115                 120

<210> SEQ ID NO 11
<211> LENGTH: 122
<212> TYPE: PRT
<213> ORGANISM: Artificial Sequence
<220> FEATURE:
<223> OTHER INFORMATION: huVH7

<400> SEQUENCE: 11

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Arg Gly Gly Asp Tyr Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Ala Ile Thr Gly Gly Trp Ala Met Asp Tyr Trp
            100                 105                 110

Gly Gln Gly Thr Leu Val Thr Val Ser Ser
        115                 120

<210> SEQ ID NO 12
<211> LENGTH: 122
<212> TYPE: PRT
<213> ORGANISM: Artificial Sequence
<220> FEATURE:
<223> OTHER INFORMATION: huVH8

<400> SEQUENCE: 12

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Arg Gly Gly Asp Tyr Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Tyr Ala Met Asp Tyr Trp
            100                 105                 110

Gly Gln Gly Thr Leu Val Thr Val Ser Ser
        115                 120

<210> SEQ ID NO 13
<211> LENGTH: 122
<212> TYPE: PRT
<213> ORGANISM: Artificial Sequence

```
<220> FEATURE:
<223> OTHER INFORMATION: huVH9

<400> SEQUENCE: 13

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Arg Gly Gly Asp Tyr Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Phe Ala Met Asp Tyr Trp
            100                 105                 110

Gly Gln Gly Thr Leu Val Thr Val Ser Ser
        115                 120

<210> SEQ ID NO 14
<211> LENGTH: 122
<212> TYPE: PRT
<213> ORGANISM: Artificial Sequence
<220> FEATURE:
<223> OTHER INFORMATION: huVH10

<400> SEQUENCE: 14

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Arg Gly Gly Asp Tyr Thr Tyr Tyr Pro Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Ala Ala Met Asp Tyr Trp
            100                 105                 110

Gly Gln Gly Thr Leu Val Thr Val Ser Ser
        115                 120

<210> SEQ ID NO 15
<211> LENGTH: 122
<212> TYPE: PRT
<213> ORGANISM: Artificial Sequence
<220> FEATURE:
<223> OTHER INFORMATION: huVH11

<400> SEQUENCE: 15

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30
```

```
Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Trp Ala Leu Asp Tyr Trp
            100                 105                 110

Gly Gln Gly Thr Leu Val Thr Val Ser Ser
            115                 120
```

<210> SEQ ID NO 16
<211> LENGTH: 122
<212> TYPE: PRT
<213> ORGANISM: Artificial Sequence
<220> FEATURE:
<223> OTHER INFORMATION: huVH12

<400> SEQUENCE: 16

```
Glu Val Arg Leu Met Ala Ser Gly Gly Gly Leu Val Gln Pro Gly Gly
 1               5                  10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Trp Ala Phe Asp Tyr Trp
            100                 105                 110

Gly Gln Gly Thr Leu Val Thr Val Ser Ser
            115                 120
```

<210> SEQ ID NO 17
<211> LENGTH: 122
<212> TYPE: PRT
<213> ORGANISM: Artificial Sequence
<220> FEATURE:
<223> OTHER INFORMATION: huVH13

<400> SEQUENCE: 17

```
Glu Val Arg Leu Met Ala Ser Gly Gly Gly Leu Val Gln Pro Gly Gly
 1               5                  10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Arg Arg Val Ser Met Ile Thr Gly Gly Trp Ala Ile Asp Tyr Trp
            100                 105                 110

Gly Gln Gly Thr Leu Val Thr Val Ser Ser
            115                 120

<210> SEQ ID NO 18
<211> LENGTH: 122
<212> TYPE: PRT
<213> ORGANISM: Artificial Sequence
<220> FEATURE:
<223> OTHER INFORMATION: huVH14

<400> SEQUENCE: 18

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Glu Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Trp Ala Met Asp Tyr Trp
            100                 105                 110

Gly Gln Gly Thr Leu Val Thr Val Ser Ser
            115                 120

<210> SEQ ID NO 19
<211> LENGTH: 122
<212> TYPE: PRT
<213> ORGANISM: Artificial Sequence
<220> FEATURE:
<223> OTHER INFORMATION: huVH15

<400> SEQUENCE: 19

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Trp Ala Met Asp Tyr Trp
            100                 105                 110

Gly Gln Gly Thr Leu Val Thr Val Ser Ser
            115                 120

<210> SEQ ID NO 20
<211> LENGTH: 122
<212> TYPE: PRT
<213> ORGANISM: Artificial Sequence

```
<220> FEATURE:
<223> OTHER INFORMATION: huVH16

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Arg Gly Gly Asp Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Phe Ile Thr Gly Gly Tyr Ala Phe Asp Tyr Trp
            100                 105                 110

Gly Gln Gly Thr Leu Val Thr Val Ser Ser
        115                 120

<210> SEQ ID NO 21
<211> LENGTH: 122
<212> TYPE: PRT
<213> ORGANISM: Artificial Sequence
<220> FEATURE:
<223> OTHER INFORMATION: huVH18

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
        35                  40                  45

Ala Thr Ile Ser Arg Gly Gly Asp Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Val Ser Met Ile Thr Gly Gly Tyr Ala Met Asp Tyr Trp
            100                 105                 110

Gly Gln Gly Thr Leu Val Thr Val Ser Ser
        115                 120

<210> SEQ ID NO 22
<211> LENGTH: 122
<212> TYPE: PRT
<213> ORGANISM: Artificial Sequence
<220> FEATURE:
<223> OTHER INFORMATION: huVH20

<400> SEQUENCE: 22

Glu Val Arg Leu Met Ala Ser Gly Gly Gly Leu Val Gln Pro Gly Gly
1               5                   10                  15

Ser Leu Arg Leu Ser Cys Ala Ala Ser Glu Phe Thr Phe Ser Asn Tyr
            20                  25                  30
```

```
Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Val Ser Phe Ile Thr Gly Gly Tyr Ala Met Asp Tyr Trp
            100                 105                 110

Gly Gln Gly Thr Leu Val Thr Val Ser Ser
        115                 120

<210> SEQ ID NO 23
<211> LENGTH: 122
<212> TYPE: PRT
<213> ORGANISM: Artificial Sequence
<220> FEATURE:
<223> OTHER INFORMATION: huVH21

<400> SEQUENCE: 23

Glu Val Arg Leu Met Ala Ser Gly Gly Gly Leu Val Gln Pro Gly Gly
 1               5                  10                  15

Ser Leu Arg Leu Ser Cys Ala Ala Ser Glu Phe Thr Phe Ser Asn Tyr
            20                  25                  30

Ala Met Ser Trp Val Arg Gln Ala Pro Gly Lys Gly Leu Glu Trp Val
            35                  40                  45

Ala Thr Ile Ser Arg Gly Gly Asp Tyr Thr Tyr Tyr Pro Glu Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Arg Val Ser Phe Ile Thr Gly Gly Tyr Ala Met Asp Tyr Trp
            100                 105                 110

Gly Gln Gly Thr Leu Val Thr Val Ser Ser
        115                 120

<210> SEQ ID NO 24
<211> LENGTH: 112
<212> TYPE: PRT
<213> ORGANISM: Artificial Sequence
<220> FEATURE:
<223> OTHER INFORMATION: huVL1

<400> SEQUENCE: 24

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Ile Val Asp Ile
            20                  25                  30

Thr Gly Asn Thr Tyr Leu Glu Trp Tyr Gln Gln Arg Pro Gly Gln Ser
            35                  40                  45

Pro Arg Leu Leu Ile Tyr Lys Val Phe Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Val Gly Val Tyr Tyr Cys Phe Gln Asp
                85                  90                  95

Ser Phe Val Pro Tyr Thr Phe Gly Gln Gly Thr Lys Leu Glu Ile Lys
            100                 105                 110
```

<210> SEQ ID NO 25
<211> LENGTH: 112
<212> TYPE: PRT
<213> ORGANISM: Artificial Sequence
<220> FEATURE:
<223> OTHER INFORMATION: huVL2

<400> SEQUENCE: 25

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Asp Ile
            20                  25                  30

Thr Gly Asn Thr Tyr Leu Glu Trp Phe Gln Gln Arg Pro Gly Gln Ser
        35                  40                  45

Pro Arg Leu Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Asp
                85                  90                  95

Ser Phe Val Pro Tyr Thr Phe Gly Gln Gly Thr Lys Leu Glu Ile Lys
            100                 105                 110
```

<210> SEQ ID NO 26
<211> LENGTH: 112
<212> TYPE: PRT
<213> ORGANISM: Artificial Sequence
<220> FEATURE:
<223> OTHER INFORMATION: huVL3

<400> SEQUENCE: 26

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Asp Ile
            20                  25                  30

Thr Gly Asn Thr Tyr Leu Glu Trp Tyr Gln Gln Arg Pro Gly Gln Ser
        35                  40                  45

Pro Arg Arg Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Asp
                85                  90                  95

Ser Phe Val Pro Tyr Thr Phe Gly Gln Gly Thr Lys Leu Glu Ile Lys
            100                 105                 110
```

<210> SEQ ID NO 27
<211> LENGTH: 112
<212> TYPE: PRT
<213> ORGANISM: Artificial Sequence
<220> FEATURE:
<223> OTHER INFORMATION: huVL4

```
<400> SEQUENCE: 27

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Asp Ile
            20                  25                  30

Thr Gly Asn Thr Tyr Leu Glu Trp Tyr Gln Gln Arg Pro Gly Gln Ser
        35                  40                  45

Pro Arg Leu Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Glu
                85                  90                  95

Ser Phe Val Pro Tyr Thr Phe Gly Gln Gly Thr Lys Leu Glu Ile Lys
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: huVL5

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Asp Ile
            20                  25                  30

Thr Gly Asn Thr Tyr Leu Glu Trp Tyr Gln Gln Arg Pro Gly Gln Ser
        35                  40                  45

Pro Arg Leu Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Asp
                85                  90                  95

Thr Phe Val Pro Tyr Thr Phe Gly Gln Gly Thr Lys Leu Glu Ile Lys
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: huVL6

<400> SEQUENCE: 29

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Asp Ile
            20                  25                  30

Thr Gly Asn Thr Tyr Leu Glu Trp Phe Gln Gln Arg Pro Gly Gln Ser
        35                  40                  45

Pro Arg Arg Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Phe Gln Glu
            85                  90                  95

Ser Phe Val Pro Tyr Thr Phe Gly Gln Gly Thr Lys Leu Glu Ile Lys
            100                 105                 110

<210> SEQ ID NO 30
<211> LENGTH: 330
<212> TYPE: PRT
<213> ORGANISM: Homo sapiens

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

```
<210> SEQ ID NO 31
<211> LENGTH: 107
<212> TYPE: PRT
<213> ORGANISM: Homo sapiens

<400> SEQUENCE: 31

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 32
<211> LENGTH: 122
<212> TYPE: PRT
<213> ORGANISM: Mus musculus

<400> SEQUENCE: 32

Glu Val Arg Leu Met Ala Ser Gly Gly Gly Leu Val Lys Pro Gly Gly
1               5                   10                  15

Ser Leu Lys Leu Ser Cys Ala Ala Ser Glu Phe Thr Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Arg Gly Gly Asp Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Arg Val Ser Met Ile Thr Gly Gly Trp Ala Met Asp Tyr Trp
            100                 105                 110

Gly Gln Gly Thr Ser Val Thr Val Ser Ser
        115                 120

<210> SEQ ID NO 33
<211> LENGTH: 122
<212> TYPE: PRT
<213> ORGANISM: Artificial Sequence
<220> FEATURE:
<223> OTHER INFORMATION: cVH2

<400> SEQUENCE: 33

Glu Val Arg Leu Leu Ala Ser Gly Gly Gly Leu Val Lys Pro Gly Gly
1               5                   10                  15

Ser Leu Lys Leu Ser Cys Ala Ala Ser Glu Phe Thr Phe Ser Asn Tyr
            20                  25                  30

Ala Met Ser Trp Val Arg Gln Thr Pro Glu Lys Arg Leu Glu Trp Val
        35                  40                  45
```

Ala Thr Ile Ser Arg Gly Gly Asp Tyr Thr Tyr Tyr Pro Asp Ser Val
            50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Leu Tyr Tyr Cys
                 85                  90                  95

Ala Arg Arg Val Ser Met Ile Thr Gly Gly Trp Ala Met Asp Tyr Trp
                100                 105                 110

Gly Gln Gly Thr Ser Val Thr Val Ser Ser
            115                 120

<210> SEQ ID NO 34
<211> LENGTH: 122
<212> TYPE: PRT
<213> ORGANISM: Artificial Sequence
<220> FEATURE:
<223> OTHER INFORMATION: cVH3

<400> SEQUENCE: 34

Glu Val Gln Leu Leu Ala Ser Gly Gly Leu Val Lys Pro Gly Gly
 1               5                  10                  15

Ser Leu Lys Leu Ser Cys Ala Ala Ser Glu Phe Thr Phe Ser Asn Tyr
                 20                  25                  30

Ala Met Ser Trp Val Arg Gln Thr Pro Glu Lys Arg Leu Glu Trp Val
             35                  40                  45

Ala Thr Ile Ser Arg Gly Gly Asp Tyr Thr Tyr Tyr Pro Asp Ser Val
            50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Leu Tyr Tyr Cys
                 85                  90                  95

Ala Arg Arg Val Ser Met Ile Thr Gly Gly Trp Ala Met Asp Tyr Trp
                100                 105                 110

Gly Gln Gly Thr Ser Val Thr Val Ser Ser
            115                 120

<210> SEQ ID NO 35
<211> LENGTH: 122
<212> TYPE: PRT
<213> ORGANISM: Artificial Sequence
<220> FEATURE:
<223> OTHER INFORMATION: cVH4

<400> SEQUENCE: 35

Glu Val Arg Leu Met Glu Ser Gly Gly Gly Leu Val Lys Pro Gly Gly
 1               5                  10                  15

Ser Leu Lys Leu Ser Cys Ala Ala Ser Glu Phe Thr Phe Ser Asn Tyr
                 20                  25                  30

Ala Met Ser Trp Val Arg Gln Thr Pro Glu Lys Arg Leu Glu Trp Val
             35                  40                  45

Ala Thr Ile Ser Arg Gly Gly Asp Tyr Thr Tyr Tyr Pro Asp Ser Val
            50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Leu Tyr Tyr Cys
                 85                  90                  95

```
Ala Arg Arg Val Ser Met Ile Thr Gly Gly Trp Ala Met Asp Tyr Trp
            100                 105                 110

Gly Gln Gly Thr Ser Val Thr Val Ser Ser
        115                 120

<210> SEQ ID NO 36
<211> LENGTH: 112
<212> TYPE: PRT
<213> ORGANISM: Artificial Sequence
<220> FEATURE:
<223> OTHER INFORMATION: cVK1

<400> SEQUENCE: 36

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Asp Ile
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Phe Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Asp
                85                  90                  95

Ser Phe Val Pro Tyr Thr Phe Gly Gly Gly Thr Lys Leu Glu Ile Lys
            100                 105                 110

<210> SEQ ID NO 37
<211> LENGTH: 112
<212> TYPE: PRT
<213> ORGANISM: Artificial Sequence
<220> FEATURE:
<223> OTHER INFORMATION: hVK2

<400> SEQUENCE: 37

Glu Val Val Met Thr Gln Ser Pro Ala Thr Leu Ser Leu Ser Pro Gly
1               5                   10                  15

Glu Arg Ala Thr Leu Ser Cys Arg Ser Ser Gln Ser Ile Val Asp Ile
            20                  25                  30

Thr Gly Asn Thr Tyr Leu Glu Trp Tyr Gln Gln Lys Pro Gly Gln Ala
        35                  40                  45

Pro Arg Leu Leu Ile Tyr Lys Val Phe Asn Arg Phe Ser Gly Ile Pro
    50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Phe Gln Asp
                85                  90                  95

Ser Phe Val Pro Tyr Thr Phe Gly Gln Gly Thr Lys Leu Glu Ile Lys
            100                 105                 110

<210> SEQ ID NO 38
<211> LENGTH: 153
<212> TYPE: PRT
<213> ORGANISM: Homo sapiens
```

<400> SEQUENCE: 38

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 39
<211> LENGTH: 107
<212> TYPE: PRT
<213> ORGANISM: Artificial Sequence
<220> FEATURE:
<223> OTHER INFORMATION: VL-146B7

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Arg Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser His
                85                  90                  95

Thr Phe Gly Gln Gly Thr Lys Leu Glu Ile Ser
            100                 105

<210> SEQ ID NO 40
<211> LENGTH: 118
<212> TYPE: PRT
<213> ORGANISM: Artificial Sequence
<220> FEATURE:
<223> OTHER INFORMATION: VH-146B7

<400> SEQUENCE: 40

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr Thr Tyr
            20                  25                  30

```
Trp Ile Gly Trp Val Arg Gln Met Pro Gly Lys Gly Leu Glu Tyr Met
            35                  40                  45
Gly Ile Ile Tyr Pro Gly Asp Ser Asp Thr Arg Tyr Ser Pro Ser Phe
50                  55                  60
Gln Gly Gln Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
            85                  90                  95
Ala Arg Gly Gly Asn Trp Asn Cys Phe Asp Tyr Trp Gly Gln Gly Thr
                100                 105                 110
Leu Val Thr Val Ser Ser
        115

<210> SEQ ID NO 41
<211> LENGTH: 11
<212> TYPE: PRT
<213> ORGANISM: Artificial Sequence
<220> FEATURE:
<223> OTHER INFORMATION: VL CDR3 DISC0280

<400> SEQUENCE: 41

Ala Trp Tyr Asp Arg Glu Leu Ser Glu Trp Val
1               5                   10

<210> SEQ ID NO 42
<211> LENGTH: 16
<212> TYPE: PRT
<213> ORGANISM: Artificial Sequence
<220> FEATURE:
<223> OTHER INFORMATION: VH CDR3 DISC0280

<400> SEQUENCE: 42

Asp Pro Ala Ala Trp Pro Leu Gln Gln Ser Leu Ala Trp Phe Asp Pro
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: IL-15 peptide fragment stretch

<400> SEQUENCE: 43

Asp Thr Val Glu Asn Leu Ile Ile Leu Ala Asn Asn
1               5                   10
```

ANTIBODIES TO IL-15

CROSS-REFERENCE TO RELATED APPLICATION

This application is the U.S. national stage application of International Patent Application No. PCT/EP2015/064931, filed Jul. 1, 2015.

FIELD OF THE INVENTION

The present invention relates to antibodies that bind interleukin-15 and are, in particular, able to neutralize the activity of said protein, as well as to uses thereof as therapeutics.

BACKGROUND OF THE INVENTION

Interleukin 15 (IL-15), also known as MGC9721, is a 14 to 15 kDa pro-inflammatory cytokine which is expressed in multiple tissues (placenta, skeletal muscle, kidney, lung, heart, monocytes/macrophages) and numerous cell types including monocytes and macrophages, blood derived dendritic cells, epithelial and fibroblast cells, through various stimulatory conditions (Fenhiger and Caligiuri, 2001, *Blood*, 97(1):14-32). Interleukin-15 regulates T and natural killer (NK) cell activation, survival and proliferation. This cytokine and interleukin 2 (IL-2) share many biological activities, consistent with their shared receptor signaling components (IL-2/15Rβ and IL-2/15Rγc). However, specificity for IL-15 versus IL-2 is provided by unique private α-chain receptor that completes the IL-15Rαβγ heterotrimeric high-affinity receptor complex and thereby allows differential responsiveness depending on the ligand and high-affinity receptor expressed (Fenhiger and Caligiuri, 2001, supra). In addition, while soluble IL-15 is capable of directly stimulating cells expressing either the IL-15Rαβγ high-affinity receptor or the lower affinity IL-15Rβγ receptor, a phenomenon described as IL-15 cis presentation, it was suggested that IL-15 bound to IL-15Rα for example at the surface of one cell type could associate with and stimulate through the IL-15Rβγ expressed at the surface of another cell, a phenomenon described as IL-15 trans presentation (Stonier et al, 2010, *Immunol. Lett.*, 127:85-92). Since in the circulation IL-15 may also be preferentially associated with soluble IL-15Rα, this trans presentation mechanism is unlikely restricted to cell-cell interactions (Bergamaschi et al, 2012, *Blood* 120:e1-e8).

A deleterious role for a dysregulation of IL-15 expression has been suggested in several disorders including autoimmune diseases such as rheumatoid arthritis, psoriasis and celiac disease, as well as in malignancies such as T cell leukemias. In particular, IL-15 triggers an anti-apoptotic pathway in human intraepithelial lymphocytes that is believed to be a potential new target in celiac disease-associated inflammation and lymphomagenesis (Malamut et. al., 2010, *J. Clin. Invest.*, 120(6):2131-43). Further, it has been found that IL-15 expression is increased in human eosinophilic esophagitis and mediates similar/related pathogenesis in mice (Zhu et al., 2010, *Gastroenterology*, 139(1): 182-93). In addition, it has been found that in the observed increased proinflammatory activity in patients with Alzheimer's disease and frontotemporal dementia, IL-15 can be used as a marker since its levels are elevated in cerebrospinal fluid of those patients (Rentzos et al., 2006, *J. Geriatr. Psychiatry Neurol.*, 19(2):114-7).

IL-15 has also been found to play a role of central importance in activating innate immune cells, in particular NK and T cells in transplant rejection response, in particular in the case of allograft transplants (Ferrari-Lacraz et al., 2011, *J Immunol.*, 167(6): 3478-3485).

IL-15 is also believed to be a myokine, playing various roles in muscle and fat metabolism (Raschke and Eckel, 2013, *Mediators Inflamm.*, 320724). Excess of pro-inflammatory cytokines including IL-15 has been linked to wasting, hypermetabolic syndromes observed during trauma, injury, and cachexia associated with cancer (Martinez-Hernandez et al., 2012, *Oncol Rep.*, 28(4):1443-52).

While it is generally considered to have anti-tumor activities through stimulation of the immune system, IL-15 has also been suggested to play detrimental roles in certain forms of cancers such as acute lymphoid leukemia and large granular lymphocytic leukemia, in addition to its abovementioned role in celiac disease-associated lymphomagenesis (Cario et al., 2007, *J Clin Oncol.* 25(30):4813-20).

Therefore, it would be beneficial to provide potent and specific antibodies that could bind IL-15 and neutralize its biological activities for therapeutic applications, in particular for the treatment of IL-15 related disorders, notably auto-immune and inflammatory disorders.

A fully human monoclonal anti-IL-15 antibody (146B7) has been disclosed (Villadsen et al., 2003, *J. Clin. Invest.*, 112: 1571-1580) as not competing with IL-15 for binding its IL-15Rα receptor but potently interfering with the assembly of the IL-15 receptor α, β, γ complex. In a human psoriasis xenograft model, antibody 146B7 reduced the severity of psoriasis. In a phase I-II dose-escalation trial with antibody 146B7 (also known as AMG 714) in patients with active rheumatoid arthritis, improvements in disease activity have been observed (Baslund et al, 2005, *Arthritis & Rheumatism*, 52(9): 2686-2692). However, this program was discontinued for lack of efficacy (Fulmer 2009, *T. SciBX* 2(36)).

A monoclonal mouse anti-IL-15 antibody (B-E29) has been disclosed as preventing IL-15 binding to IL-15Rα (Bernard et al., 2004, *J. Biol. Chem.*, 279(23): 24313-34322). A fully human anti-IL-15 antibody (DISC0280) has been disclosed as preventing IL-15 binding to IL-15Rα even more potently and efficiently than B-E29 when directly compared (Finch et al., 2011, *Brit. J. Pharmacol.*, 162:480-490). While DISC0280 was very potent and efficient at neutralizing IL-15 activity in vitro, it failed to do so in vivo. It was therefore hypothesized that preventing binding of IL-15 to IL-15Rα could be detrimental for in vivo IL-15 neutralizing activity.

Despite the existence of anti-IL-15 antibodies in the prior art, there remains a need for developing alternative anti-IL-15 antibodies which exhibit advantageous properties in comparison to the antibodies of the prior art and/or are more efficiently and/or more easily produced.

The present invention fulfills this need by providing novel humanized antibodies specific for IL-15 deriving from mouse B-E29 antibody which do not prevent binding of IL-15 to IL-15Rα, can neutralize IL-15 in vivo and are more potent and efficient at binding and neutralizing IL-15 than the 146B7 antibody.

SUMMARY OF THE INVENTION

The present invention is mainly directed towards antibodies which bind interleukin-15, in particular human IL-15, comprising the variable regions described herewith which derive from the humanization and optimization of a mouse anti-IL-15 antibody.

A first aspect of the invention provides an isolated antibody binding IL-15 comprising:
  (1) a heavy chain variable region of SEQ ID NO: 5 or any variant thereof wherein 1, 2, 3, 4, 5, 6, 7, 8, or 9 amino acids of said sequence are substituted by a different amino acid, and
  (2) a light chain variable region of SEQ ID NO: 24 or any variant thereof wherein 1, 2, 3, 4, 5, 6, 7, 8, 9, or 10 amino acids of said sequence are substituted by a different amino acid,
  or an antigen-binding fragment thereof.

A second aspect of the invention relates to an isolated nucleic acid molecule encoding said antibody or fragment thereof.

A third and fourth aspects of the invention relate to a recombinant expression vector comprising said nucleic acid molecule, and to a host cell comprising said recombinant vector, respectively.

A fifth aspect of the invention relates to a process for producing antibodies as described herewith comprising culturing a host cell transformed with an expression vector comprising a nucleic acid sequence that encodes said antibodies under conditions sufficient to promote expression of said antibodies or fragments thereof.

A sixth aspect of the invention provides a pharmaceutical composition comprising one or more of (i) an isolated antibody binding IL-15 or antigen-binding fragment thereof, (ii) a nucleic acid, (iii) a vector, and/or (iv) a host cell, as described herewith, and at least one pharmaceutically acceptable carrier.

A seventh aspect of the invention relates to an imaging composition or a diagnosis composition comprising one or more anti-IL-15 antibody as described herewith.

An eighth aspect of the invention is a kit comprising one or more anti-IL-15 antibody as described herewith.

A ninth aspect of the invention relates to an antibody or formulation thereof according to the invention for use in the prevention and/or treatment of IL-15 related disorders such as an autoimmune disease and/or inflammatory disorder, a malignancy, transplant rejection, a metabolic condition (such as hypermetabolic condition) and/or an infectious disease caused by parasitic, viral or bacterial pathogens.

A tenth aspect relates to a method of preventing and/or treating IL-15 related disorders such as an autoimmune disease and/or inflammatory disorder, a malignancy, transplant rejection, a metabolic condition (such as hypermetabolic condition) inherited or related to trauma, injury or cancer and/or an infectious disease caused by parasitic, viral or bacterial pathogens comprising administering in a subject in need thereof a therapeutically effective amount of said antibody or said pharmaceutical composition. Other features and advantages of the invention will be apparent from the following detailed description.

DESCRIPTION OF THE FIGURES

FIG. 1. Alignment of sequences of variable regions of humanized and chimeric variants of mouse B-E29, compared to comparative antibody 1, B-E29. (A) Heavy chain variable regions: "cVH1" (SEQ ID NO: 32) represents the heavy chain variable region of mouse B-E29 antibody; "cVH2" (SEQ ID NO: 33), "cVH3" (SEQ ID NO: 34) and "cVH4" (SEQ ID NO: 35) are variants of cVH1; "hVH1" is a humanized form of cVH1. (B) Light chain variable regions: "cVK1" (SEQ ID NO: 36) represents the light chain variable region of mouse B-E29 antibody; "hVK1" (SEQ ID NO: 24), "hVK2" (SEQ ID NO: 37) are two humanized forms of cVK1. CDRs as defined by Kabat are underligned and key residues important for the VH/VL interface and canonical loop structure are asterisked (*).

DETAILED DESCRIPTION OF THE INVENTION

Definitions

Figure 2:
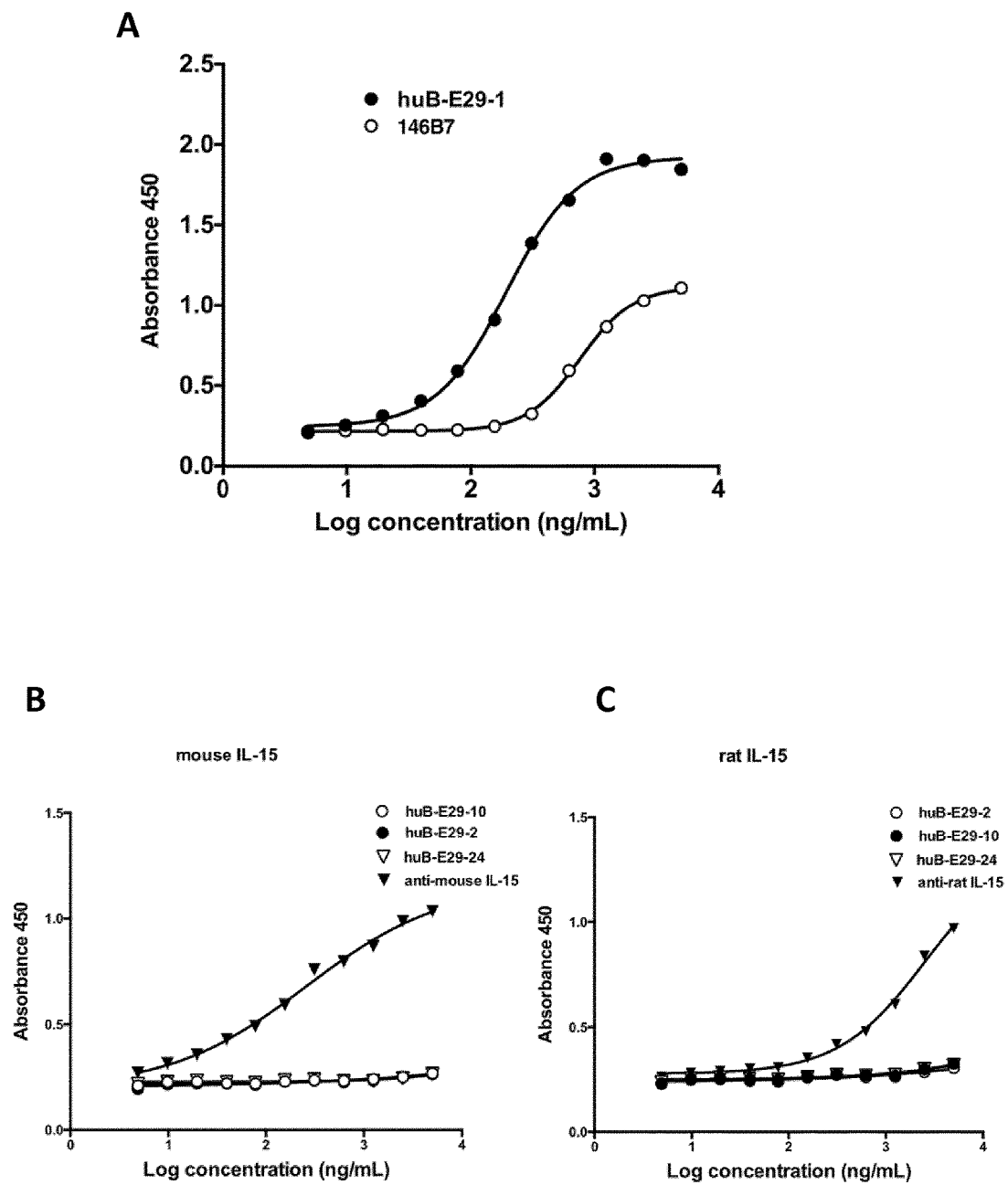
FIG. 2. Dose-response curves of the binding of anti-IL-15 antibodies to human IL-15 as determined by ELISA, expressed as absorbance at 450 nm. Binding of one exemplary anti-IL-15 antibody of the invention (huB-E29-1) and 146B7 antibody to human IL-15 (A), binding of various recombinant anti-IL-15 antibodies to recombinant mouse IL-15 (B) or rat IL-15 (C).

The terms "interleukin 15", "interleukin-15", "IL-15", designate herewith the interleukin 15 protein, also known as MGC9721, that is a 14 to 15 kDa pro-inflammatory cytokine that, in humans is encoded by the IL-15 gene whose sequence is disclosed under Hugo Gene Nomenclature Committee ID 5977. The immature form of IL-15 comprises 162 amino acids, where the first 29 amino acids constitute the signal peptide, and the amino acids 30 to 48 constitute the pro-peptide. The immature form of IL-15 is available under UniProtKB accession number P40933. The mature form of the IL-15 protein corresponds to amino acids Asn 49 to Ser 162, where the indicated positions correspond to the amino acid positions on the immature IL-15 amino acid sequence. The amino acid sequence of human mature IL-15 corresponds to SEQ ID NO: 1. The amino acid sequences of immature IL-15 from other species are available in the art and include, for instance, mouse IL-15 (UniProtKB accession number P48346, corresponding to mature IL-15 form of SEQ ID NO: 2), rat IL-15 (UniProtKB accession number P97604, corresponding to mature IL-15 form of SEQ ID NO: 3), Rhesus macaque IL-15 (UniProtKB accession NP_001038196, XP_001091166, XP_001091289 XP_001091416, corresponding to mature IL-15 form of SEQ ID NO: 4) and Cynomolgus monkey IL-15 (predicted sequence from NCBI accession number XP_005556036.1, corresponding to mature IL-15 form of SEQ ID NO: 4). The term "interleukin 15" also includes any variants or isoforms of interleukin 15 which are naturally expressed by cells. Of note, two alternatively spliced transcript variants of IL-15 have been reported. Although both isoforms produce the same mature protein, they differ in their cellular trafficking.

The term "antibody" as referred to herein designates a polypeptide that binds an antigen. This includes whole antibodies and any antigen-binding fragments. The term "antibody" is used in its broadest sense and includes monoclonal antibodies, polyclonal antibodies, human antibodies, humanized antibodies, chimeric antibodies, and further engineered antibodies as long as the characteristic properties of the invention are retained, in particular the ability of binding the target antigen (such as IL-15), and optionally the same epitope of IL-15 as the one recognized by the antibodies of the invention. Examples of antibodies and fragments thereof include a variable domain fragment ("Fv", consisting of the VH and VL domains of a single arm of an antibody), Fab fragment (monovalent fragment consisting of the VH, VL, CH1 and CL domains), Fab$_2$ fragment (bivalent), Fab$_3$ fragment (trivalent), Fab' fragment (Fab with hinge region), F(ab')$_2$ fragment (bivalent fragment including two Fab fragments linked by a disulfide bridge at the hinge region), Fd fragment (consisting of the VH and CH1 domains), rIgG (reduced IgG or half-IgG), diabodies, triabodies, tetrabodies, minibodies, domain antibodies (dAb), monovalent antibodies, divalent or multivalent antibodies comprising a fragment of more than one antibody, single chain variable fragment (ScFv), bis-scFv (bispecific), and derivatives of antibodies such as disulfide stabilized Fv fragments, CDR-comprising peptides, as well as epitope-binding fragments of any of the above (Holliger and Hudson, 2005, *Nature Biotechnology*, 23(9): 1126-1136). An antibody refers to a glycoprotein comprising at least two heavy (H) chains and two light (L) chains inter-connected by disulfide bonds, or an antigen-binding fragment thereof. Each heavy chain comprises a heavy chain variable region (VH) and a heavy chain constant region (CH). Each light chain comprises a light chain variable region (VL) and a light chain constant region (CL). In mammalians, the heavy chain can either be alpha ($\alpha$), delta ($\delta$), epsilon ($\epsilon$), gamma ($\gamma$) or mu ($\mu$), which defines the class of antibody IgA, IgD, IgE, IgG and IgM, respectively. In mammalians, the light chain can either be lambda ($\lambda$) or kappa ($\kappa$). In mammalians, depending on the class of antibody, the heavy chain constant region comprises three immunoglobulin domains, CH1, CH2, and CH3 (for IgA, IgD, IgG) or four immunoglobulin domains, CH1, CH2, CH3, and CH4 (for IgE and IgM). The light chain constant region comprises one immunoglobulin domain, CL. An antibody can have the structure of an IgA, IgG, IgE, IgD and IgM as well as any subtype thereof. Antibodies may be from any source including in particular primate (human and non-human primate) and primatized sources.

The term "variable domain" (variable domain of a light chain (VL), variable domain of a heavy chain (VH)) as used herein refers to each of the pair of light and heavy chain domains which are involved directly in binding the antibody to the antigen. The variable light and heavy chain domains have the same general structure and each domain comprises four framework ("FW") regions whose sequences are widely conserved, connected by three "hypervariable regions" called "complementary determining regions" or "CDRs". The framework regions adopt a $\beta$-sheet conformation and the CDRs may form loops connecting the $\beta$-sheet structure. The CDRs in each chain are held in their three-dimensional structure by the framework regions and form together with the CDRs from the other chain the antigen binding site. The term "antigen-binding portion of an antibody" when used herein refers to the amino acid residues of an antibody which are responsible for antigen-binding. The antigen-binding portion of an antibody comprises amino acid residues from the "complementary determining regions" or "CDRs". "Framework" or "FW" regions are those variable domain regions other than the hypervariable region residues as herein defined. Therefore, the light and heavy chain variable domains of an antibody comprise from N- to C-terminus: the domains FW1, CDR1, FW2, CDR2, FW3, CDR3, and FW4. The residues of the CDR and FW regions are conventionally numbered according to the standard definition of Kabat et al (*Sequences of Proteins of Immunological Interest*, 5th ed., Public Health Service, National Institutes of Health, Bethesda, Md. (1991), Publication No. 91-3242). This numbering system is used in the present specification except where otherwise indicated. The Kabat residue designations do not always correspond directly to the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35 (CDR-H1), residues 50-65 (CDR-H2) and residues 95-102 (CDR-H3) according to the Kabat numbering system. The CDRs of the light chain variable domain are located at residues 24-34 (CDR-L1), residues 50-56 (CDR-L2) and residues 89-97 (CDR-L3) according to the Kabat numbering system.

In the present application, unless specified otherwise, for all human immunoglobulin heavy and light chain variable domains, numbering is according to the "Kabat numbering system" (*Sequences of Proteins of Immunological Interest*, 5th ed., Public Health Service, National Institutes of Health, Bethesda, Md. (1991), Publication No. 91-3242).

In the present application, unless specified otherwise, for all human immunoglobulin heavy chain constant domains, numbering is according to the "EU numbering system" (Edelman et al, 1969, *Proc Natl Acad Sci*, 63(1): 78-85).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "chimeric antibody" generally refers to an antibody comprising a variable region from one source or species and at least a portion of a constant region derived from a different source or species, usually prepared by recombinant DNA techniques. A typical example of chimeric antibodies includes those comprising a mouse variable region and a human constant region. As defined herewith this term also includes an antibody comprising at least one of the CDRs of a first human antibody and at least a portion of a constant region of a second human antibody. It also includes an antibody comprising heavy chain CDR1, CDR2, and CDR3 of a first human antibody and light chain CDR1, CDR2, and CDR3 of a second human antibody.

The term "humanized antibody" designates antibodies from a non-human species having one or more complementarity determining regions (CDRs) from said non-human species and a framework region from a human immunoglobulin molecule. Humanized antibodies may optionally further comprise one or more framework residues derived from the non-human species from which the CDRs were derived.

The term "human antibody" or "fully human antibody" refers to antibodies in which the variable regions and the constant regions of both the heavy and the light chains are all of human origin, or substantially identical to sequences of human origin, but not necessarily from the same antibody.

The term "isolated antibody" refers to an antibody that has been separated from a component of its natural environment. For instance, an isolated antibody has been purified to greater than 95% or 99% purity as determined by methods in the art (see e.g. Flatman et al, 2007, *J Chromatogr B Analyt Technol Biomed Life Sci*, 848: 79-87) including electrophoretic (e.g. SDS-PAGE, isoelectric focusing, capillary electrophoresis) or chromatographic (e.g. ion exchange or reverse phase HPLC (high performance liquid chromatography) methods.

The terms "polynucleotide" or "nucleic acid molecule" refers to a polymer comprising nucleotides. Examples of nucleic acid molecules include DNA, RNA, locked nucleic acid (LNA), complementary DNA (cDNA).

"Polypeptide" is understood as a peptide, an oligopeptide, an oligomer or a protein comprising at least two amino acids joined to each other by a normal or modified peptide bond, such as in the cases of the isosteric peptides, for example. A polypeptide can be composed of amino acids other than the 20 amino acids defined by the genetic code. A polypeptide can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the lateral chain or even at the carboxy- or amino-terminal ends. For example, polypeptide modifications is understood to include acetylation, acylation, ADP-ribosylation, amidation, covalent fixation of flavine, covalent fixation of heme, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, cysteine formation, pyroglutamate formation, formylation, gamma-carboxylation, glycosylation including pegylation, GPI anchor formation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (*Proteins Structure and Molecular Properties* (1993) 2$^{nd}$ Ed., T. E. Creighton, New York; *Post-translational Covalent Modifications of Proteins* (1983) B. C. Johnson, Ed., Academic Press, New York; Seifter et al. (1990) *Analysis for protein modifications and nonprotein cofactors, Meth. Enzymol.* 182: 626-646 and Rattan et al., (1992) *Protein Synthesis: Post-translational Modifications and Aging, Ann NY Acad Sci*, 663: 48-62).

"Isolated polynucleotide" or "isolated polypeptide" is understood as a polynucleotide or a polypeptide such as previously defined which is isolated from the human body or otherwise produced by a technical process.

The term "variant" can apply to a polynucleotide and/or a polypeptide. For instance, a variant of a peptide or polypeptide, as referred to herein means a peptide or polypeptide substantially homologous to the referenced peptide sequence, but which has an amino acid sequence different from that of the referenced sequence because of one or more amino acid deletions, insertions and/or substitutions. Substantially homologous means a variant amino acid sequence which is identical to the referenced peptide sequence except for the deletion, insertion and/or substitution of a few amino acids, e.g. 1, 2, 3, 4, 5, or 6 amino acids. Substantially homologous means a variant amino acid sequence that is at least 80%, at least 85%, at least 90%, at least 91%, at least 92%, at least 93%, at least 94%, at least 95%, at least 96%, at least 97%, at least 98% or at least 99% identical to the referenced amino acid sequence. A variant nucleic acid sequence can be at least 80%, at least 85%, at least 90%, at least 91%, at least 92%, at least 93%, at least 94%, at least 95%, at least 96%, at least 97%, at least 98% or at least 99% identical to the referenced nucleic acid sequence. The identity of two amino acid sequences or of two nucleic acid sequences can be determined by visual inspection and/or mathematical calculation, or more easily by comparing sequence information using known computer program used for sequence comparison such as Clustal package version 1.83. A variant may comprise a sequence having at least one conservatively substituted amino acid, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known (Kyte, et al, 1982, *J. Mol. Biol.*, 157: 105-131). For example, a "conservative amino acid substitution" may involve a substitution of a native amino acid residue with a non-native residue such that there is little or no effect on the polarity or charge of the amino acid residue at that position. Alternatively, substitutions for one or more amino acids present in the original polypeptide are not conservative, which may generate a variant with modified properties compared to the antibody of reference. Desired amino acid substitutions (whether conservative or non-conservative) can be determined by those skilled in the art at the time such substitutions are desired. The term "variant" also includes a peptide or polypeptide substantially homologous to the referenced peptide sequence, but which has an amino acid sequence different from that of the referenced sequence because one or more amino acids have been chemically modified or substituted by amino acid analogs. This term also includes glycosylated polypeptides. The term "epitope" includes any polypeptide determinant capable of specific binding to an antibody. In certain embodiments, epitope determinant includes chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

As used herewith the term "bind" or "binding" of an antibody to a target antigen means an at least temporary interaction or association of said antibody with, or to, said target antigen (such as IL-15) or with, or to, fragments of said target antigen comprising an epitope recognized by said antibody. As used herewith, an antibody binding IL-15 is also called an anti-IL-15 antibody.

The terms "selectively binds", "specifically binds", "specific for", when applied to an antibody, indicate that the antibody preferentially recognizes and/or binds the target polypeptide or epitope, i.e. with a higher affinity than to any other antigen or epitope, i.e. the binding to the target polypeptide can be discriminated from non-specific binding to other antigens. The binding affinity of an antibody can be readily determined by one of ordinary skill in the art, for example, by equilibrium dialysis, equilibrium binding, surface plasmon resonance or spectroscopy (e.g. using a fluorescence assay).

Especially, when using the surface plasmon resonance (SPR) technology, biomolecular binding events cause changes in the refractive index at a surface layer where one of the binding partner is immobilized, which are detected as changes in the surface plasmon resonance signal expressed as response units (RU). By measuring the real-time binding kinetics of an antibody to its target antigen, the SPR technology can determine how fast is the association between the antibody and its target (measured as $k_a$ or $k_{on}$ association constant), how strong is its association (measured as $k_d$ or $k_{off}$ dissociation constant). The affinity of an antibody for its target can be quantitatively measured by determining its equilibrium dissociation constant, $K_D$, defined as $K_D=k_d/k_a$ where $k_a$ is the association rate ($k_{on}$) and $k_d$ the dissociation rate ($k_{off}$) (Murphy, et al, 2006, *Curr Protoc Protein Sci*, Chapter 19: Unit 19.14). Comparison of affinity and/or binding properties between two antibodies can be established without actually determining the $K_D$ value for each antibody, but based on a quantitative measurement of binding (e.g. by ELISA or FACS analysis) that is proportional to $K_D$ or a qualitative measurement of affinity or an inference of affinity (e.g. in functional assay or in vitro or in vivo assay). The term "blocking" or "neutralizing" activity of an antibody refers to its ability to inhibit its target's activity. The neutralizing activity of an antibody may be determined by in vitro assays or in vivo assays or functional assays. Applied to an antibody binding IL-15, this term refers to the antibody's ability to generally neutralize IL-15 activity, which can correspond for instance to the inhibition of the IL-15-induced proliferation and/or survival of activated T cells, natural killer cells, natural killer T cells and B lymphocytes or any other cell expressing the heterotrimeric IL-15Rαβγ or the heterodimeric IL-15Rβγ receptor (Finch, et al, 2011, *Br J Pharmacol.* 162:480-90), the IL-15-induced immunoglobulin synthesis by B lymphocytes stimulated by anti-IgM or CD40 ligand (Litinskiy et al, 2012, *Nat Immunol.*, 3:822-9), the IL-15 induced activation of human neutrophils (Rathhe and Girard, 2004, *J Leukoc Biol.*, 76:162-8), and the IL-15-induced production of proinflammatory cytokines from macrophages, dendritic cells or epithelial cells (Nanayakkara, et al, 2013, *Am J Clin Nutr.*, 98:1123-35). In particular, the neutralizing activity of the anti-IL-15 antibodies can be evaluated by measuring their ability to inhibit IL-15-induced proliferation and/or survival of cell lines such as Kit 225 or M-07e cells as described in the example section. Since IL-15 can directly, and alone, act on cells expressing the heterotrimeric IL-15Rαβγ or the heterodimeric IL-15Rβγ receptor (cis signalling) or when already bound to IL-15Rα receptor (trans signalling) (Stonier, et al, 2010, supra), an antibody binding to IL-15 could neutralize either, or both, cis and trans presentation of IL-15. The "potency" of an antibody may be expressed as the concentration of antibody/antigen-binding fragment which produces the half-maximal effect at a given antigen concentration. For example, the "effect" of an antibody may be inhibition or neutralization of its target's activity. In this case, the antibody concentration producing the half-maximal inhibition may be referred to as $IC_{50}$, which is given in mol/l or M. If binding is the measured "effect" of an antibody, such as in an ELISA assay, the half-maximal binding capacity ($BC_{50}$) of such an antibody may be expressed as the concentration of antibody which produces the half-maximal signal at a given antigen concentration, which is given in mol/l or M. Potency is usually influenced by affinity until, at a given antigen concentration, an affinity is reached beyond which further improvements in affinity will not enhance binding of the antigen anymore (so-called potency ceiling). Applied to an antibody against IL-15, potency may, for example, be determined by measuring the $IC_{50}$ value of IL-15 induced proliferation and/or survival of cell lines such as Kit 225 or M-07e cells in presence of the antibody, or the $BC_{50}$ value for binding to IL-15 from different sources or species.

The term "effector function" as used herein includes a biochemical event that results from the interaction of an antibody Fc region with an Fc receptor or ligand. Effector functions include FcγR-mediated effector functions such as ADCC (antibody dependent cell-mediated cytotoxicity) and ADCP (antibody dependent cell-mediated phagocytosis), and complement-mediated effector functions such as CDC (complement dependent cytotoxicity). An effector function of an antibody may be modified by altering, i.e. enhancing or reducing, preferably enhancing, the affinity of the antibody for an effector molecule such as an Fc receptor or a complement component. Binding affinity of an antibody Fc region with an Fc receptor or ligand can be altered by modifying the effector molecule binding site. It is also possible that an alteration in the binding site on the antibody for the effector molecule alters the geometry of the interaction without significantly altering the overall binding affinity, rendering the effector mechanism ineffective as in non-productive binding. It is also possible to alter an effector function by modifying a site not directly involved in effector molecule binding, but otherwise involved in performance of the effector function. By altering an effector function of an antibody it may be possible to control various aspects of the immune response, e.g. enhancing or suppressing various reactions of the immune system, with possible beneficial effects in diagnosis and therapy.

The term "pharmaceutically acceptable" refers to a carrier comprised of a material that is not biologically or otherwise undesirable.

The term "carrier" refers to any components present in a pharmaceutical formulation other than the active agent and thus includes diluents, binders, lubricants, disintegrants, fillers, coloring agents, wetting or emulsifying agents, pH buffering agents, preservatives and the like.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it for example based on familial history; (b) inhibiting the disease, i.e., arresting its development; or (c) relieving the disease, i.e., causing regression of the disease and/or its symptoms or conditions such as improvement or remediation of damage. For instance, treatment of celiac disease comprises preventing, decreasing or even eradicating the symptoms of the disease or disorder, for instance partial or total alleviation of abdominal pain, diarrhea, unintended weight loss, malabsorption syndrome, and of abnormalities of the intestinal mucosa such as villous atrophy, erosions, ulcers and infiltration by normal or abnormal intra-epithelial lymphocytes.

The terms "IL-15 related diseases and/or disorders" encompass diseases and disorders characterized by an overexpression of IL-15 and/or increased levels and/or abnormal IL-15 expression by a cell or organ, and/or abnormal expression of a IL-15 variant by a cell or organ. Such diseases and disorders encompass for example autoimmune diseases and/or inflammatory disorders, such as disorders having a pro-inflammatory IL-15 related component and malignancies.

The terms "autoimmune diseases and/or inflammatory disorders" are generally defined herewith as diseases or disorders arising from an abnormal immune response of the subject's body against substances and tissues normally present in the body and inflammatory abnormalities which may or may not involve the immune system, respectively. Non-limitative examples of autoimmune diseases and inflammatory disorders include mostly rheumatoid arthritis, psoriasis, celiac disease, in particular refractory celiac disease, sarcoidosis, inflammatory bowel disease (e.g. ulcerative colitis, Crohn's disease), hepatitis C-induced liver diseases, multiple sclerosis, auto-immune hepatitis, primary biliary cirrhosis, sclerosing cholangitis, biliary atresia, alopecia areata, transplant rejection response, inflammatory diseases of the central nervous system, and eosinophilic esophagitis.

The term "malignancies" mostly cover herewith T-cell leukemia, such as cutaneous T-cell lymphoma (CTCL) (e.g. mycosis fungoides, Sezary syndrome), lymphoproliferative disorder of granular lymphocytes (LDGL), large granular lymphocytic leukemia, and acute lymphocytic leukemia (ALL), but also pre-B cell leukemia, osteosarcoma, Ewing sarcoma, rhabdomyosarcoma, melanoma, small cell lung cancer, renal cell carcinoma, glioblastoma, neuroblastoma, and mesothelioma. The terms "infectious disease caused by parasitic, viral or bacterial pathogens" mostly cover herewith granulomatous infections (such as tuberculosis, leishmaniasis, schistosomiasis, and cytomegalovirus infections) and hantaviruses infections (such as hantavirus haemorrhagic fever with renal syndrome and hantavirus pulmonary syndrome).

The term "inflammatory diseases of the central nervous system (CNS)" relates to disorders characterized by an inflammation of the CNS, in particular amyloid related disorders. Non-limitative examples of those disorders are Alzheimer's disease, Parkinson's disease and Huntington's disease.

The term "metabolic diseases" mostly cover diabetes, muscular dystrophy and hypermetabolic conditions.

The term "hypermetabolic condition" mostly covers inherited conditions such as sickle cell disease or acquired hypermetabolic conditions such as those related to trauma, infection or cancer-associated cachexia.

The term "subject" as used herein refers to mammals. For example, mammals contemplated by the present invention include human, primates, domesticated animals such as cattle, sheep, pigs, horses, laboratory rodents and the like.

The term "efficacy" of a treatment or method according to the invention can be measured based on changes in the course of disease or condition in response to a use or a method according to the invention. For example, the efficacy of a treatment or method according to the invention can be measured by its impact on signs or symptoms of illness. A response is achieved when the patient experiences partial or total alleviation, or reduction of unwanted symptoms of illness.

The term "effective amount" as used herein refers to an amount of at least one antibody according to the invention, or a pharmaceutical formulation thereof, that elicits a detectable reduction of the symptoms of the disease in a subject that is being administered said antibody.

Anti-IL-15 Antibodies

General Characteristics of the Antibodies Binding IL-15

In a first aspect, the present invention provides antibodies, or antigen-binding fragments thereof, that bind to IL-15, in particular human IL-15, or a fragment of IL-15, and comprise at least one heavy chain variable region and/or at least one light chain variable region of an antibody as described herewith.

In one embodiment of the invention are provided isolated antibodies binding IL-15, more particularly antibodies specific for IL-15, in particular human IL-15, or antigen-binding fragments thereof, comprising at least one heavy chain variable region and at least one light chain variable region, and optionally at least one fragment of a constant region, as described herewith.

Generally, the antigen-binding fragment of the antibody according to the invention comprises CDR1, FW2, CDR2, FW3, CDR3 and FW4 of the heavy chain and/or light chain variable regions of said antibody.

In one embodiment, the antigen-binding fragment of the antibody according to the invention comprises amino acids 26 to 111 of SEQ ID NO: 5 or a variant thereof, and/or amino acids 24 to 102 of SEQ ID NO: 24 or a variant thereof.

The protein to which the antibodies according to the invention, or fragments thereof, bind can be the IL-15 protein of any species.

The antibodies according to the present invention generally exhibit a high specificity for human IL-15. However, depending on the degree of sequence identity between IL-15 homologs of different species, a given antibody or antigen-binding fragment may show cross-reactivity with IL-15 from at least one other species, e.g. monkey (e.g. Cynomolgus monkey, Rhesus macaque), mouse, rat, marmoset, dog, and/or rabbit. For antibodies directed towards human IL-15, some level of cross-reactivity with other mammalian forms of IL-15 may be desirable in certain circumstances, for example when testing antibodies in animal models of a particular disease or for conducting toxicology, safety and dosage studies.

In a specific embodiment, the antibodies according to the invention or fragments thereof bind preferentially to human IL-15.

In another embodiment, the antibodies according to the invention or antigen-binding fragments thereof show cross-reactivity with human IL-15, Cynomolgus monkey IL-15, and Rhesus macaque IL-15.

In a still further embodiment, the antibodies according to the invention or antigen-binding fragments thereof show no cross-reactivity with rat IL-15 and/or mouse IL-15. In some embodiments, the binding affinity (e.g. inversely correlated to the $K_D$ value) of antibodies, and fragments thereof, according to the invention for human IL-15 is at least 2 times, at least 5 times, at least 10 times, at least 50 times, at least 100 times, at least 500 times, or at least 1000 times higher than their binding affinity for a non-human IL-15, such as mouse or rat IL-15.

In one embodiment, the antibodies according to the invention or fragments thereof bind preferentially to IL-15 and, optionally, additionally exhibit a weak binding, or virtually no binding (i.e. negligible or not detectable binding) to other proteins having homology with IL-15 such as IL-2, in particular human IL-2 (SEQ ID NO: 38).

In some embodiments, the quantitative binding of antibodies, and fragments thereof, according to the invention for IL-15 is at least 2 times, at least 5 times, at least 10 times, at least 50 times, at least 100 times, at least 500 times, or at least 1000 times higher than their quantitative binding for IL-2.

Binding affinity and/or quantitative binding can be measured by any method known in the art including equilibrium dialysis, equilibrium binding, gel filtration, ELISA, surface plasmon resonance or spectroscopy (e.g. using a fluorescence assay) (Jiang et al. *BMC Pharmacology* 2010, 10:10) and can be expressed as, for instance, on-rate, off-rate, equilibrium dissociation constant ($K_D$), equilibrium constant (Keq) or any other term used in the art.

In some embodiments, the antibodies, and antigen-binding fragments thereof, according to the invention specifically bind to human IL-15 with an equilibrium dissociation constant ($K_D$) equal to or lower than 100 nM, in particular lower than 10 nM, more particularly lower than 1 nM, or lower than 0.5 nM, or lower than 0.1 nM, or lower than 0.01 nM, or lower than 0.005 nM.

In a particular embodiment, the antibodies according to the invention or antigen-binding fragments thereof inhibit IL-15 activity and, optionally, additionally exhibit a weak inhibitory activity, or virtually no inhibitory activity (i.e. negligible or not detectable activity) towards other proteins having homology with IL-15, such as IL-2.

The ability of an antibody to block or neutralize the activity of its target protein can be evaluated by its potency as defined herewith, which is itself reflected, for instance, by the $IC_{50}$ value. Typically, the neutralizing activity of an antibody may be determined by in vitro assays, such as an assay for measuring the level of inhibition of IL-15-induced proliferation and/or survival of cell lines such as Kit 225 or M-07e cells, in the presence of said antibody, as described in the example section.

In some embodiments, the antibodies, and antigen-binding fragments thereof, according to the invention have a $IC_{50}$ equal to or lower than 200 nM, in particular lower than 100 nM, in particular lower than 50 nM, lower than 30 nM, lower than 20 nM, more particularly lower than 10 nM, lower than 8 nM, lower than 7 nM, lower than 5 nM, lower than 4 nM, lower than 3 nM, lower than 2 nM, lower than 1 nM, lower than 0.5 nM, lower than 0.3 nM, lower than 0.2 nM, lower than 0.1 nM, lower than 0.05 nM, or lower than 0.03 nM, for inhibiting IL-15 activity such as IL-15 induced proliferation and/or survival of cell lines such as Kit 225 or M-07e cells as described in the example section.

It is understood that any variant of an antibody according to the invention, or fragment thereof, that is described herewith is able to bind IL-15 and optionally neutralize IL-15 activity. In a particular embodiment, such variant can show the same or even higher binding affinity for IL-15 and/or the same or even higher potency and/or the same or greater species-selectivity and/or the same or greater selectivity for IL-15, and/or the same or greater neutralizing efficacy, in comparison to the parental antibody or fragment from which said variant derives.

In another particular embodiment, the antibodies according to the invention or antigen-binding fragments thereof do not substantially prevent the binding of IL-15 to IL-15Rα, i.e. the inhibition of binding of IL-15 to IL-15Rα in presence of the antibodies according to the invention is negligible or not detectable.

The antibodies according to the invention can be monoclonal antibodies, polyclonal antibodies, human antibodies, humanized antibodies, chimeric antibodies, and further engineered antibodies as long as the characteristic properties of the antibodies of the invention are retained, in particular the ability of binding to the target antigen, more specifically to the same epitope of IL-15 as the one recognized by the antibodies of the invention, and optionally the ability of neutralizing IL-15 activity.

In a particular embodiment of the invention, the antibodies to IL-15 according to the invention, or antigen-binding fragments thereof which bind to IL-15, are monoclonal antibodies.

In a further particular embodiment of the invention, the antibodies to IL-15 according to the invention, or antigen-binding fragments thereof which bind to IL-15, are humanized antibodies.

In a further particular embodiment of the invention, the antibodies to IL-15 according to the invention, or antigen-binding fragments thereof which bind to IL-15, are recombinant antibodies.

The antibodies to IL-15 according to the invention, or antigen-binding fragments thereof which bind to IL-15, can be characterized by their portion interacting with the target's protein, in particular by their variable region, which typically comprises a heavy chain variable region and a light chain variable region.

Characteristics of the Anti-IL-15 Antibodies in Relation to their Variable Regions In one embodiment, the invention relates to an isolated antibody binding IL-15 comprising:
(1) a heavy chain variable region of SEQ ID NO: 5 or any variant thereof wherein 1, 2, 3, 4, 5, 6, 7, 8, or 9 amino acids of said sequence are substituted by a different amino acid, and
(2) a light chain variable region of SEQ ID NO: 24 or any variant thereof wherein 1, 2, 3, 4, 5, 6, 7, 8, 9, or 10 amino acids of said sequence are substituted by a different amino acid,
or an antigen-binding fragment thereof.

In a particular embodiment, the invention relates to an isolated antibody binding IL-15 comprising:
(1) a heavy chain variable region of SEQ ID NO: 5 or any variant thereof having at least 95%, at least 96%, at least 97%, at least 98%, or at least 99% identity with SEQ ID NO: 5, and (2) a light chain variable region of SEQ ID NO: 24 or any variant thereof having at least 95%, at least 96%, at least 97%, at least 98%, or at least 99% identity with SEQ ID NO: 24, or an antigen-binding fragment thereof.

In a more particular embodiment, the antibody according to the invention comprises:

(1) a heavy chain variable region having at least 96% identity with SEQ ID NO: 5, and (2) a light chain variable region having at least 98% identity with SEQ ID NO: 24, or an antigen-binding fragment thereof.

In a still more particular embodiment, the antibody according to the invention comprises:

(1) a heavy chain variable region having at least 97% identity with SEQ ID NO: 5, and (2) a light chain variable region having at least 99% identity with SEQ ID NO: 24 or an antigen-binding fragment thereof.

In one embodiment according to the invention, said variant of SEQ ID NO: 5 has the amino acid sequence of SEQ ID NO: 5 except that at least one, in particular 1, 2, 3, 4, or 5, of the amino acids:

(i) arginine (R) at position H3 (VH RH3), methionine (M) at position H5 (VH MH5), alanine (A) at position H6 (VH AH6), alanine (A) at position H49 (VH AH49), within the heavy chain variable framework region, and/or (ii) aspartic acid (D) at position H61 (VH DH61), serine (S) at position H62 (VH SH62), within the heavy chain CDR2, and/or (iii) methionine (M) at position H98 (VH MH98), tryptophan (W) at position H100C (VH WH100C), methionine (M) at position H100E (VH MH100E), within the heavy chain CDR3, are substituted by a different amino acid.

In a still further embodiment, said variant of SEQ ID NO: 5 has the amino acid sequence of SEQ ID NO: 5 except that:

(i) VH RH3 is substituted by glutamine (Q), and/or VH MH5 is substituted by valine (V), and/or VH AH6 is substituted by glutamic acid (E), and/or VH AH49 is substituted by serine (S), and/or (ii) VH DH61 is substituted by glutamic acid (E), and/or VH SH62 is substituted by threonine (T), and/or (iii) VH MH98 is substituted by leucine (L), phenylalanine (F), isoleucine (I), or alanine (A), and/or VH WH100C is substituted by tyrosine (Y), phenylalanine (F), or alanine (A), and/or VH MH100E is substituted by leucine (L), phenylalanine (F), or isoleucine (I).

In one embodiment of the invention, said variant of SEQ ID NO: 24 has the amino acid sequence of SEQ ID NO: 24 except that at least one, in particular 1, 2, 3, or 4, of the amino acids:

(i) tyrosine (Y) at position L36 (VL YL36), leucine (L) at position L46 (VL LL46), within the light chain variable framework region, and/or (ii) aspartic acid (D) at position L91 (VL DL91), serine (S) at position L92 (VL SL92), within the light chain CDR3, are substituted by a different amino acid.

In a still further embodiment, said variant of SEQ ID NO: 24 has the amino acid sequence of SEQ ID NO: 24 except that:

(i) VL YL36 is substituted by phenylalanine (F), and/or VL LL46 is substituted by arginine (R), and/or (ii) VL DL91 is substituted by glutamic acid (E), and/or VL SL92 is substituted by threonine (T).

In another embodiment, the antibody according to the invention, or antigen-binding fragment thereof, comprises:

(1) a heavy chain variable region of amino acid sequence of SEQ ID NO: 5 except that:

(i) VH RH3 is substituted by glutamine (Q), and/or VH MH5 is substituted by valine (V), and/or VH AH6 is substituted by glutamic acid (E), and/or (ii) VH SH62 is substituted by threonine (T), and/or (iii) VH WH100C is substituted by tyrosine (Y), and (2) a light chain variable region of amino acid sequence of SEQ ID NO: 24.

In a more particular embodiment, the antibody according to the invention, or antigen-binding fragment thereof, comprises:

(i) a heavy chain variable region selected from: SEQ ID NO: 5, SEQ ID NO: 6, SEQ ID NO: 12, SEQ ID NO: 21, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 22 and SEQ ID NO: 23, and (ii) a light chain variable region selected from: SEQ ID NO: 24, SEQ ID NO: 25, SEQ ID NO: 26, SEQ ID NO: 27, SEQ ID NO: 28, and SEQ ID NO: 29.

In a more particular embodiment, the antibody according to the invention, or antigen-binding fragment thereof, comprises a heavy chain variable region of SEQ ID NO: 6. In a more particular embodiment, the antibody according to the invention, or antigen-binding fragment thereof, comprises a light chain variable region of SEQ ID NO: 24. Specific examples of the antibodies according to the invention include those listed in Table 1.

TABLE 1

| Antibody name | VH region | SEQ ID NO: | VL region | SEQ ID NO: |
|---|---|---|---|---|
| huB-E29-1 | huVH1 | NO: 5 | huVL1 | NO: 24 |
| huB-E29-2 | huVH2 | NO: 6 | huVL1 | NO: 24 |
| huB-E29-3 | huVH3 | NO: 7 | huVL1 | NO: 24 |
| huB-E29-4 | huVH1 | NO: 5 | huVL2 | NO: 25 |
| huB-E29-5 | huVH1 | NO: 5 | huVL3 | NO: 26 |
| huB-E29-6 | huVH4 | NO: 8 | huVL1 | NO: 24 |
| huB-E29-7 | huVH5 | NO: 9 | huVL1 | NO: 24 |
| huB-E29-8 | huVH6 | NO: 10 | huVL1 | NO: 24 |
| huB-E29-9 | huVH7 | NO: 11 | huVL1 | NO: 24 |
| huB-E29-10 | huVH8 | NO: 12 | huVL1 | NO: 24 |
| huB-E29-11 | huVH9 | NO: 13 | huVL1 | NO: 24 |
| huB-E29-12 | huVH10 | NO: 14 | huVL1 | NO: 24 |
| huB-E29-13 | huVH11 | NO: 15 | huVL1 | NO: 24 |
| huB-E29-14 | huVH12 | NO: 16 | huVL1 | NO: 24 |
| huB-E29-15 | huVH13 | NO: 17 | huVL1 | NO: 24 |
| huB-E29-16 | huVH14 | NO: 18 | huVL1 | NO: 24 |
| huB-E29-17 | huVH15 | NO: 19 | huVL1 | NO: 24 |
| huB-E29-18 | huVH1 | NO: 5 | huVL4 | NO: 27 |
| huB-E29-19 | huVH1 | NO: 5 | huVL5 | NO: 28 |
| huB-E29-22 | huVH16 | NO: 20 | huVL6 | NO: 29 |
| huB-E29-24 | huVH18 | NO: 21 | huVL1 | NO: 24 |
| huB-E29-30 | huVH20 | NO: 22 | huVL1 | NO: 24 |
| huB-E29-31 | huVH20 | NO: 22 | huVL6 | NO: 29 |
| huB-E29-34 | huVH21 | NO: 23 | huVL6 | NO: 29 |

In a more particular embodiment, the antibody according to the invention, or antigen-binding fragment thereof, comprises:

(1) a heavy chain variable region selected from: SEQ ID NO: 5, SEQ ID NO: 6, SEQ ID NO: 12, and SEQ ID NO: 21, and (2) a light chain variable region of SEQ ID NO: 24.

Still more particularly, the antibody according to the invention, or antigen-binding fragment thereof, comprises a heavy chain variable region of SEQ ID NO: 5 and a light chain variable region of SEQ ID NO: 24.

Still more particularly, the antibody according to the invention, or antigen-binding fragment thereof, comprises a heavy chain variable region of SEQ ID NO: 6 and a light chain variable region of SEQ ID NO: 24.

Still more particularly, the antibody according to the invention, or antigen-binding fragment thereof, comprises a heavy chain variable region of SEQ ID NO: 12 and a light chain variable region of SEQ ID NO: 24.

Still more particularly, the antibody according to the invention, or antigen-binding fragment thereof, comprises a heavy chain variable region of SEQ ID NO: 21 and a light chain variable region of SEQ ID NO: 24.

Characteristics of the Anti-IL-15 Antibodies in Relation to their Constant Region A portion corresponding to a constant region of an antibody is optionally comprised in the isolated antibodies binding IL-15, or antigen-binding fragments thereof, according to the invention.

Depending on the proposed function of the antibodies and, in particular the effector functions which may be required, a constant region of an antibody may or may not be present within the antibodies according to the invention.

Typically, when present within the antibodies or antigen-binding fragments thereof according to the invention, the heavy chain constant region or portion thereof can be from any antibody isotype. For instance, the heavy chain constant region or portion thereof can be that of an antibody selected from IgG (e.g. IgG1, IgG2, IgG3, IgG4), IgA (e.g. IgA1, IgA2), IgD, IgE, IgM (e.g. IgM1, IgM2). It can be, in particular, the constant region or portion thereof of an IgG, more particularly IgG1.

In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-15 activity. When present within the antibodies or antigen-binding fragments thereof according to the invention, the light chain constant region or portion thereof can be from any light chain's constant region. For instance, the light chain constant region or portion thereof can be from the kappa or lambda light chain.

In a particular aspect of the invention, the antibodies for IL-15, or antigen-binding fragments thereof, comprise (i) at least one heavy chain comprising a variable region as described herewith and a constant region or portion thereof from an IgG antibody (in particular IgG1, more particularly allotype G1m3, and (ii) at least one light chain comprising a variable region as described herewith and a constant region or portion thereof from a kappa (in particular allotype Km3) light chain. The amino acid sequence of the constant region of allotype G1m3 is SEQ ID NO: 30. The amino acid sequence of the constant region of allotype Km3 is SEQ ID NO: 31.

The antibodies, or antigen-binding fragments thereof, of the invention have at least one antigen binding site, e.g. one or two antigen binding sites.

In some embodiments, the isolated antibodies and antigen-binding fragments thereof according to the invention are glycosylated. Typically, monosaccharides such as N-acetyl-glucosamine, mannose, glucose, galactose, fucose, sialic acid, etc, are assembled to oligosaccharides at individual glycosylation sites on the antibody.

Conjugates Comprising an Auxiliary Molecule

In another aspect of the invention, the isolated antibodies or antigen-binding fragments thereof according to the invention are optionally conjugated to an accessory molecule, and are then also referred to herein as "conjugated antibodies or conjugated antibody fragments".

The accessory molecule may be conjugated to the antibody or antibody fragment directly or via a spacer of suitable length for instance as described in Kellogg et al. (2011, Bioconjug Chem, 22: 717-27).

In one embodiment, particularly adapted for therapeutic purposes, the accessory molecule can be a therapeutic effector group such as a cytotoxic (e.g. an enzymatically active toxin of bacterial, fungal, plant or animal origin, or fragment thereof), cytostatic, or immunomodulatory agent, including radioactive groups (i.e groups comprising a radionucleide or radioisotope), or small molecules.

In another embodiment, the accessory molecule comprises an antigen-binding fragment of an antibody, which, when conjugated to the antibody or antibody fragment according to the invention, form a bispecific antibody. In particular, said bispecific antibody may be directed to two different epitopes of IL-15 (hence defining a biparatopic antibody). The conjugated antibodies and conjugated antibody fragments according to the invention can target the drug in vivo to a site of disease (e.g. a site of inflammation or a tumor) such that the conjugated auxiliary molecule can have a therapeutic effect on the site of disease.

In an alternative embodiment, particularly adapted for diagnostic purposes, the accessory molecule can be, for example, a labeling group including radioisotopes (e.g. 3H, 14C, 32P, 35S, 125I), chromogenic labels, e.g. enzymes which can be used to convert a substrate to a detectable colored (e.g. horseradish peroxidase, alkaline phosphatase, β-galactosidase) or fluorescent compound (e.g. Green Fluorescent Protein, Red Fluorescent Protein), spectroscopic labels (e.g. fluorescent labels such as fluorescein and its derivatives like FITC, Texas red, cyanine dyes, photocyan, rhodamine, or labels presenting a visible color), luminescent labels including luciferins, affinity labels which may be developed by a further compound specific for the label and allowing easy detection and quantification, or any other label used in standard ELISA.

Nucleic Acids Encoding the Polypeptides of the Invention

According to another embodiment, it is provided an isolated nucleic acid molecule encoding an antibody or antigen-binding fragment thereof according to the invention. The isolated nucleic acid according to the invention may be, for instance, natural DNA or RNA or a recombinant or synthetic DNA, RNA or LNA or a recombinant nucleic acid molecule comprising any of the nucleic acid molecules according to the invention either alone or in combination. In a particular embodiment, the nucleic acid molecules according to the invention are cDNA.

In a particular embodiment, it is provided an isolated nucleic acid comprising one or more of:

(1) a nucleic acid sequence encoding a heavy chain variable region of SEQ ID NO: 5 or any variant thereof wherein 1, 2, 3, 4, 5, 6, 7, 8, or 9 amino acids of said sequence are substituted by a different amino acid, or an antigen-binding fragment thereof, and (2) a nucleic acid sequence encoding a light chain variable region of SEQ ID NO: 24 or any variant thereof wherein 1, 2, 3, 4, 5, 6, 7, 8, 9, or 10 amino acids of said sequence are substituted by a different amino acid, or an antigen-binding fragment thereof.

In a particular embodiment, it is provided an isolated nucleic acid comprising one or more of:
(1) a nucleic acid sequence encoding a heavy chain variable region of SEQ ID NO: 5 or any variant thereof having at least 95%, at least 96%, at least 97%, at least 98%, or at least 99% identity with SEQ ID NO: 5, or an antigen-binding fragment thereof, and
(2) a nucleic acid sequence encoding a light chain variable region of SEQ ID NO: 24 or any variant thereof having at least 95%, at least 96%, at least 97%, at least 98%, or at least 99% identity with SEQ ID NO: 24, or an antigen-binding fragment thereof.

In a particular embodiment, it is provided an isolated nucleic acid comprising one or more of:
(1) a nucleic acid sequence encoding a heavy chain variable region selected from: SEQ ID NO: 5, SEQ ID NO: 6, SEQ ID NO: 12, SEQ ID NO: 21, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 22 and SEQ ID NO: 23, or an antigen-binding fragment thereof, and
(2) a nucleic acid sequence encoding a light chain variable region selected from: SEQ ID NO: 24, SEQ ID NO: 25, SEQ ID NO: 26, SEQ ID NO: 27, SEQ ID NO: 28, and SEQ ID NO: 29, or an antigen-binding fragment thereof.

In a more particular embodiment, the invention provides an isolated nucleic acid comprising one or more of:
(1) a nucleic acid sequence encoding a heavy chain variable region selected from:
SEQ ID NO: 5, SEQ ID NO: 6, SEQ ID NO: 12, and SEQ ID NO: 21, and
(2) a nucleic acid sequence encoding a light chain variable region of SEQ ID NO: 24.

Vectors and Host Cells for Production and Purification of the Polypeptides of the Invention In one embodiment, the invention provides a recombinant expression vector comprising a nucleic acid molecule according to the invention, wherein the vector optionally comprises an expression control sequence, allowing expression in prokaryotic or eukaryotic host cells of the encoded polypeptide, operably linked to said nucleic acid molecule.

Numerous expression systems can be used, including without limitation chromosomes, episomes, and derived viruses. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses. These recombinant vectors can equally be cosmid or phagemid derivatives.

The nucleic acid sequence can be inserted in the recombinant vector by methods well known to a person skilled in the art such as, for example, those that are described in *MOLECULAR CLONING: A LABORATORY MANUAL*, Sambrook et al., 4$^{th}$ Ed., Cold Spring Harbor Laboratory Press, Cold Spring Harbor, N.Y., 2001.

The recombinant vector can include nucleotide sequences that control the regulation of the polynucleotide expression as well as nucleotide sequences permitting the expression and the transcription of a polynucleotide of the invention and the translation of a polypeptide of the invention, these sequences being selected according to the host cells that are used.

Thus, for example, an appropriate secretion signal can be integrated in the recombinant vector so that the polypeptide, encoded by the nucleic acid molecule of the invention, will be directed towards the lumen of the endoplasmic reticulum, towards the periplasmic space, on the membrane or towards the extracellular environment. The choice of an appropriate secretion signal may facilitate subsequent protein purification. In a further embodiment, it is provided a host cell comprising a recombinant vector according to the invention.

The introduction of the recombinant vector in a host cell can be carried out according to methods that are well known to a person skilled in the art, such as those described in BASIC METHODS IN MOLECULAR BIOLOGY, Davis et al., 2nd ed., McGraw-Hill Professional Publishing, 1995, and MOLECULAR CLONING: A LABORATORY MANUAL, supra, such as transfection by calcium phosphate, transfection by DEAE dextran, transfection, microinjection, transfection by cationic lipids, electroporation, transduction or infection.

The host cell can be, for example, bacterial cells such as *Escherichia coli* or *Streptomyces*, cells of fungi such as *Aspergillus* and yeasts such as *Saccharomyces*, insect cells, Chinese Hamster Ovary (CHO) cells, C127 mouse cell line, BHK cell line of Syrian hamster cells, Human Embryonic Kidney 293 (HEK 293) cells. In a particular embodiment, the host cell is a CHO cell or a HEK 293 cell.

The host cells can be used, for example, to express a polypeptide of the invention. After purification by standard methods, the polypeptide of the invention can be used in a method described hereinafter.

For instance, when expression systems that secrete the recombinant protein are employed, the culture medium may first be concentrated using a commercially available protein concentration filter, for example, an Amicon or Millipore Pellicon ultrafiltration unit. Following the concentration step, the concentrate can be applied to a purification matrix such as a gel filtration matrix. Alternatively, an anion exchange and/or an affinity resin can be employed. The matrices can be acrylamide, agarose, dextran, cellulose or other types commonly employed in protein purification. Alternatively, a cation exchange step can be employed. Finally, one or more reversed-phase high performance liquid chromatography (RP-HPLC) steps employing hydrophobic RP-HPLC media can be employed to further purify the antibodies or fragments thereof. Some or all of the foregoing purification steps, in various combinations, are well known and can be employed to provide a substantially homogeneous recombinant protein.

Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Microbial cells can be disrupted by any convenient method, including freeze-thaw cycling, sonication, mechanical disruption, or use of cell lysing agents.

In another embodiment, the invention provides a process for producing cells capable of expressing a polypeptide according to the invention, comprising genetically engineering cells with a recombinant expression vector or a nucleic acid according to the invention.

In another embodiment, the invention provides a process for producing antibodies or fragments thereof according to the invention comprises culturing a host cell transformed with an expression vector comprising a nucleic sequence that encodes said antibodies or fragments thereof under conditions sufficient to promote expression of said polypeptides. The antibody or fragment thereof according to the invention is then recovered from culture medium or cell extracts, depending upon the expression system employed. As known to the skilled artisan, procedures for purifying a recombinant protein will vary according to such factors as the type of host cells employed and whether or not the recombinant protein is secreted into the culture medium as described above.

Compositions

The invention provides pharmaceutical or therapeutic agents as compositions and methods for treating a patient, preferably a mammalian patient, and most preferably a human patient who is suffering from a medical disorder, and in particular an IL-15 related disease or disorder such as an autoimmune disease and/or inflammatory disorder, a malignancy, transplant rejection, metabolic condition and/or an infectious disease caused by parasitic, viral or bacterial pathogens. Alternatively, the invention provides methods for preventing a medical disorder, and in particular an IL-15 related disease or disorder such as an autoimmune disease and/or inflammatory disorder, a malignancy, transplant rejection, metabolic condition and/or an infectious disease caused by parasitic, viral or bacterial pathogens.

In one embodiment, is provided a pharmaceutical composition comprising one or more of: (i) an antibody binding to IL-15 or antigen-binding fragment thereof according to the invention, (ii) a nucleic acid according to the invention, (iii) a vector according to the invention, and/or (iv) a host cell according to the invention, and at least one pharmaceutically acceptable carrier.

Pharmaceutical compositions of the invention can contain one or more antibodies binding IL-15 or antigen-binding fragments thereof in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, freeze-dried forms, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Compositions of this invention may be liquid formulations including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agent include, but are not limited to, sorbitol syrup, methylcellulose, glucose/sugar syrup, gelatin, hydroxyethylcellulose, carboxymethylcellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's The Science and Practice of Pharmacy*, 22$^{nd}$ Edition, 2012, Pharmaceutical Press and the University of the Sciences, Philadelphia College of Pharmacy, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate.

Tablets may be coated according to methods well known in the art.

Injectable compositions are typically based upon injectable sterile saline or phosphate-buffered saline or other injectable carriers known in the art.

Compositions of this invention may also be formulated as transdermal formulations comprising aqueous or non-aqueous vehicles including, but not limited to, creams, ointments, lotions, pastes, medicated plaster, patch, or membrane.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

The compounds of this invention can also be administered in sustained release forms or from sustained release drug delivery systems. A description of representative sustained release materials can also be found in the incorporated materials in *Remington's Pharmaceutical Sciences*.

Injectable formulations are particularly appropriate for administering the compositions according to the invention.

In another embodiment, the invention provides an imaging composition or diagnostic composition comprising an antibody binding IL-15 or an antigen-binding fragment thereof as described herewith.

The imaging composition or diagnostic composition according to the invention is useful for detecting elevated levels of IL-15 associated with an autoimmune disease and/or inflammatory disorder, a malignancy, transplant rejection, metabolic condition and/or an infectious disease caused by parasitic, viral or bacterial pathogens.

Combination

According to the invention, an antibody binding IL-15 or an antigen-binding fragment thereof according to the invention can be administered alone or in combination with a co-agent useful in the prevention and/or treatment of an autoimmune disease and/or inflammatory disorder, a malignancy, transplant rejection, metabolic condition and/or an infectious disease caused by parasitic, viral or bacterial pathogens, for example immune modulatory drugs including biologics, small molecules, and vaccines.

Alternatively, an antibody for IL-15 or an antigen-binding fragment thereof according to the invention can be administered or in combination with a co-agent useful in the treatment of cancer, for example an anti-cancerous drug such as cytotoxic drugs, tyrosine kinase inhibitors imatinib (Gleevec/Glivec) or gefitinib (Iressa), and therapeutic antibodies such as trastuzumab (Herceptin) or anti-CD20 antibody rituximab (Rituxan).

The invention encompasses the administration of an antibody for IL-15 or an antigen-binding fragment thereof wherein the antibody or fragment thereof is administered to an individual prior to, simultaneously or sequentially with other therapeutic regimens or co-agents useful in the prevention and/or treatment of an IL-15 related disease or disorder such as an autoimmune disease and/or inflammatory disorder, a malignancy, transplant rejection, metabolic condition and/or an infectious disease caused by parasitic, viral or bacterial pathogens, in a therapeutically effective amount. The antibody for IL-15 or an antigen-binding fragment thereof according to the invention that are administered simultaneously with said co-agents can be administered in the same or different compositions and in the same or different routes of administration. In a particular embodiment, an antibody for IL-15 or an antigen-binding fragment thereof according to the invention can be administered in combination with a compound lowering intestinal inflammation, and/or protecting intestinal mucosa, and/or lowering the immune reactivity of gluten peptides, and/or modifying the gut microbiota for the treatment of subjects suffering from celiac disease.

In a particular embodiment, an antibody for IL-15 or an antigen-binding fragment thereof according to the invention can be administered in combination with a compound lowering intestinal inflammation, and/or protecting intestinal mucosa, and/or lowering the immune reactivity of gluten peptides, and/or modifying the gut microbiota for the treatment of subjects suffering from refractory celiac disease.

Mode of Administration

Compositions of this invention may be administered in any manner including, but not limited to, orally, parenterally, sublingually, transdermally, rectally, transmucosally, topically, via inhalation, via buccal or intranasal administration or intra bladder, or combinations thereof.

Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well a slow controlled i.v. infusion. In a particular embodiment, an antibody for IL-15 or antigen-binding fragment thereof according to the invention is administered systemically or locally.

In a particular embodiment, an antibody for IL-15 or antigen-binding fragment thereof according to the invention is administered by subcutaneous or intravenous route.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Typically, therapeutically effective amounts of a pharmaceutically active antibody range from 0.5 mg/kg up to 50 mg/kg body weight dose. If the regimen is a continuous infusion, it may be in the range of 0.250 mg/kg up to 13 mg/kg of body weight.

Patients

In an embodiment, patients according to the invention are patients suffering from an IL-15 related disease or disorder such as autoimmune disease and/or inflammatory disorder including rheumatoid arthritis, psoriasis, celiac disease such as refractory celiac disease, sarcoidosis, inflammatory bowel disease (e.g. ulcerative colitis, Crohn's disease), hepatitis C-induced liver diseases, multiple sclerosis, auto-immune hepatitis, primary biliary cirrhosis, sclerosing cholangitis, biliary atresia, alopecia areata, transplant rejection response, inflammatory diseases of the central nervous system, and eosinophilic esophagitis and metabolic conditions such as hypermetabolic conditions.

In a particular embodiment, patients according to the invention are patients suffering from celiac disease.

In a particular embodiment, patients according to the invention are patients suffering from refractory celiac disease.

In a particular embodiment, patients according to the invention are patients suffering from eosinophilic esophagitis.

In a particular embodiment, patients according to the invention are patients suffering from auto-immune hepatitis.

In another embodiment, patients according to the invention are patients suffering from a malignancy including T-cell leukemia, such as cutaneous T-cell lymphoma (CTCL) (e.g. mycosis fungoides, Sezary syndrome), lymphoproliferative disorder of granular lymphocytes (LDGL), large granular lymphocytic leukemia, and acute lymphocytic leukemia (ALL), pre-B cell leukemia, osteosarcoma, Ewing sarcoma, rhabdomyosarcoma, melanoma, small cell lung cancer, renal cell carcinoma, glioblastoma, neuroblastoma, and mesothelioma.

In a particular embodiment, patients according to the invention are patients suffering from large granular lymphocytic leukemia.

In a particular embodiment, patients according to the invention are patients suffering from acute lymphocytic leukemia.

In another embodiment, patients according to the invention are patients suffering from a transplant rejection.

In a particular embodiment, patients according to the invention are patients suffering from an infectious disease caused by parasitic, viral or bacterial pathogens.

In a particular embodiment, patients according to the invention are patients suffering from an infectious disease caused by Hantavirus (Hantaan virus) such as hantavirus hemorrhagic fever with renal syndrome and/or hantavirus pulmonary syndrome.

In a still other embodiment, patients according to the invention are patients suffering from a hypermetabolic condition including sickle cell disease and cancer-associated cachexia.

In a still other embodiment, patients according to the invention are patients suffering from inflammatory diseases of the central nervous system.

In a still other embodiment, patients according to the invention are patients suffering from amyloid related disorders such as Alzheimer's disease.

Uses and Methods According to the Invention

The antibody binding IL-15 or antigen-binding fragment thereof, the nucleic acids, the vectors, the host cells, the compositions according to the invention are for use in the diagnosis, prevention or treatment of disorders associated with, caused by, or accompanied by elevated levels of IL-15 and/or elevated IL-15 activity.

In one embodiment is provided an antibody to IL-15 or antigen-binding fragment thereof according to the invention for use as a medicament.

Another embodiment provides an antibody or fragment thereof according to the invention for use in the prevention and/or treatment of an IL-15 related disease or disorder such as an autoimmune disease and/or inflammatory disorder, in particular rheumatoid arthritis, psoriasis, celiac disease, such as refractory celiac disease, sarcoidosis, inflammatory bowel disease (e.g. ulcerative colitis, Crohn's disease), hepatitis C-induced liver diseases, multiple sclerosis, auto-immune hepatitis, primary biliary cirrhosis, sclerosing cholangitis, biliary atresia, alopecia areata, transplant rejection response, inflammatory diseases of the central nervous system, and eosinophilic esophagitis.

Another embodiment provides an antibody or fragment thereof according to the invention for use in the prevention and/or treatment of a malignancy, in particular T-cell leukemia, such as cutaneous T-cell lymphoma (CTCL) (e.g. mycosis fungoides, Sezary syndrome), lymphoproliferative disorder of granular lymphocytes (LDGL), large granular lymphocytic leukemia, and acute lymphocytic leukemia (ALL), pre-B cell leukemia, osteosarcoma, Ewing sarcoma, rhabdomyosarcoma, melanoma, small cell lung cancer, renal cell carcinoma, glioblastoma, neuroblastoma, and mesothelioma.

A still other embodiment provides an antibody or fragment thereof according to the invention for use in the prevention and/or treatment of transplant rejection, a metabolic condition (such as a hypermetabolic condition) and/or an infectious disease caused by parasitic, viral or bacterial pathogens.

In one embodiment is provided a use of an antibody for IL-15 or antigen-binding fragment thereof according to the invention for the preparation of a pharmaceutical composition for preventing and/or treating an IL-15 related disease or disorder such as an autoimmune disease and/or inflammatory disorder, in particular rheumatoid arthritis, psoriasis, celiac disease, such as refractory celiac disease, sarcoidosis, inflammatory bowel disease (e.g. ulcerative colitis, Crohn's disease), hepatitis C-induced liver diseases, multiple sclerosis, auto-immune hepatitis, primary biliary cirrhosis, sclerosing cholangitis, biliary atresia, alopecia areata, inflammatory diseases of the central nervous system, and eosinophilic esophagitis.

In a specific embodiment is provided a use of an antibody for IL-15 or antigen-binding fragment thereof according to the invention for the preparation of a pharmaceutical composition for preventing and/or treating celiac disease, in particular refractory celiac disease.

In a particular embodiment, is provided a use of an antibody for IL-15 or antigen-binding fragment thereof according to the invention for the preparation of a pharmaceutical composition for preventing and/or treating eosinophilic esophagitis. In a particular embodiment, is provided a use of an antibody for IL-15 or antigen-binding fragment thereof according to the invention for the preparation of a pharmaceutical composition for preventing and/or treating auto-immune hepatitis.

In one embodiment is provided a use of an antibody for IL-15 or antigen-binding fragment thereof according to the invention for the preparation of a pharmaceutical composition for preventing and/or treating a malignancy, in particular T-cell leukemia such as acute lymphocytic leukemia, large granular lymphocytic leukemia, cutaneous T-cell lymphoma (CTCL) (e.g. mycosis fungoides, Sezary syndrome), and lymphoproliferative disorder of granular lymphocytes (LDGL), pre-B cell leukemia, osteosarcoma, Ewing sarcoma, rhabdomyosarcoma, melanoma, small cell lung cancer, renal cell carcinoma, glioblastoma, neuroblastoma, and/or mesothelioma.

In an alternative embodiment is provided a use of an antibody for IL-15 or antigen-binding fragment thereof according to the invention for the preparation of a pharmaceutical composition for preventing and/or treating large granular lymphocytic leukemia.

In an alternative embodiment is provided a use of an antibody for IL-15 or antigen-binding fragment thereof according to the invention for the preparation of a pharmaceutical composition for preventing and/or treating acute lymphocytic leukemia.

In a specific embodiment is provided a use of an antibody for IL-15 or antigen-binding fragment thereof according to the invention for the preparation of a pharmaceutical composition for preventing and/or treating transplant rejection, a metabolic condition and/or an infectious disease caused by parasitic, viral or bacterial pathogens.

In a specific embodiment is provided a use of an antibody for IL-15 or antigen-binding fragment thereof according to the invention for the preparation of a pharmaceutical composition for preventing and/or treating hantaviruses infections.

In a specific embodiment is provided a use of an antibody for IL-15 or antigen-binding fragment thereof according to the invention for the preparation of a pharmaceutical composition for preventing and/or treating an inflammatory disease of the central nervous system.

In a specific embodiment is provided a use of an antibody for IL-15 or antigen-binding fragment thereof according to the invention for the preparation of a pharmaceutical composition for preventing and/or treating Alzheimer's disease.

In another embodiment is provided a method for preventing and/or treating an IL-15 related disease or disorder such as an autoimmune disease and/or inflammatory disorder, in particular rheumatoid arthritis, psoriasis, celiac disease, in particular refractory celiac disease, sarcoidosis, inflammatory bowel disease (e.g. ulcerative colitis, Crohn's disease), hepatitis C-induced liver diseases, multiple sclerosis, auto-immune hepatitis, primary biliary cirrhosis, sclerosing cholangitis, biliary atresia, alopecia areata, inflammatory diseases of the central nervous system, and eosinophilic esophagitis, comprising administering a therapeutically effective amount of an antibody to IL-15 or antigen-binding fragment thereof according to the invention, to a subject in need thereof.

In a particular embodiment is provided a method of preventing and/or treating celiac disease, comprising administering a therapeutically effective amount of an antibody for IL-15 or antigen-binding fragment thereof according to the invention, to a subject in need thereof.

In an alternative embodiment is provided a method of preventing and/or treating a malignancy, in particular T-cell leukemia, such as acute lymphocytic leukemia, large granular lymphocytic leukemia, cutaneous T-cell lymphoma (CTCL) (e.g. mycosis fungoides, Sezary syndrome), and a lymphoproliferative disorder of granular lymphocytes (LDGL), pre-B cell leukemia, osteosarcoma, Ewing sarcoma, rhabdomyosarcoma, melanoma, small cell lung cancer, renal cell carcinoma, glioblastoma, neuroblastoma, and/or mesothelioma, comprising administering a therapeutically effective amount of an antibody to IL-15 or antigen-binding fragment thereof according to the invention, to a subject in need thereof.

In a particular embodiment is provided a method of preventing and/or treating large granular lymphocytic leukemia, comprising administering a therapeutically effective amount of an antibody to IL-15 or antigen-binding fragment thereof according to the invention, to a subject in need thereof.

In another embodiment is provided a method for preventing and/or treating transplant rejection, a metabolic condition and/or an infectious disease caused by parasitic, viral or bacterial pathogens, comprising administering a therapeutically effective amount of an antibody to IL-15 or antigen-binding fragment thereof according to the invention, to a subject in need thereof.

In an alternative embodiment is provided a method of detecting IL-15 in a biological sample comprising contacting a biological sample from a subject with an antibody to IL-15 or antigen-binding fragment thereof according to the invention.

As used herewith "biological sample" refers to cells, tissue samples or cell components (such as cellular membranes or cellular components) obtained from a subject, in particular from a subject suspected of, or suffering from, an autoimmune disease and/or inflammatory disorder, a malignancy, transplant rejection, metabolic condition and/or an infectious disease caused by parasitic, viral or bacterial pathogens, or at high risk of developing such a disorder.

Examples of biological sample include blood, serum, plasma, cerebrospinal fluid, synovial fluid, and tissue samples including cells isolated from said tissue. Tissue samples include formalin-fixed or frozen tissue sections.

Any suitable method for detection and analysis of IL-15 can be employed, including diagnostic assay techniques known in the art such as competitive binding assays, direct or indirect sandwich assays and immunoprecipitation assays conducted in either heterogeneous or homogeneous phases.

In a particular embodiment, the invention provides an ex vivo method for detecting the presence and/or concentration of IL-15 protein in a biological sample, comprising the steps of:
(i) Providing a biological sample from a subject,
(ii) Reacting said biological sample with at least one antibody or antigen-binding fragment thereof according to the invention, under conditions sufficient for binding IL-15 protein present in said biological sample to said at least one antibody or fragment thereof through antigen-antibody interactions; and
(iii) Detecting a signal proportional to the level of antigen-antibody complex formed in step (ii),
wherein the intensity of the signal correlates with the concentration of IL-15 protein in the biological sample.

More particularly, it is provided an ex-vivo method of prognosis or diagnosis of an autoimmune disease and/or inflammatory disorder, a malignancy, transplant rejection, metabolic condition and/or an infectious disease caused by parasitic, viral or bacterial pathogens, associated with an elevated level of IL-15 from a biological sample of a subject comprising the steps of:
(a) Providing a biological sample from a subject;
(b) Bringing said biological sample into contact with a solid matrix where at least one antibody or fragment thereof according to the invention is bound to, wherein the contacting is under conditions sufficient for binding Il-15 protein present in said biological fluid sample to said at least one antibody or fragment thereof through antigen-antibody interactions;
(c) Removing any unbound IL-15 protein from the surface of said solid matrix;
(d) Detecting a signal proportional to the level of antigen-antibody complex bound to said solid matrix,
(e) Comparing the level of signal detected in step (d) with the level of signal detected in the same conditions with a negative control,
wherein a level of signal detected in the subject's sample that is higher than the level of signal detected in the negative control is indicative of an elevated level of IL-15 associated with an autoimmune disease and/or inflammatory disorder, a malignancy, transplant rejection, a metabolic condition and/or an infectious disease caused by parasitic, viral or bacterial pathogens.

Kit

One aspect of the invention relates to a kit comprising at least one antibody or antigen-binding fragment thereof according to the invention, and/or at least one nucleic acid encoding said antibody or fragment thereof, and/or at least one recombinant vector comprising said nucleic acid, and/or at least one host cell according to the invention, and optionally instructional material.

In a particular embodiment, the kit according to the invention comprises at least one antibody or antigen-binding fragment thereof according to the invention, to be coupled or already coupled to a solid matrix.

Examples of solid matrix suitable for the invention include any solid phase support suitable for carrying out an immunoassay or a method according to the invention, such as beads, microparticles, nanoparticles, tubes, fabrics or plates, films, slides, wells, formed from or coated with glass, polystyrene, polypropylene, nitrocellulose, quartz, ceramic, dextran or other materials. For example, the solid matrix is in a form of microtiter wells, such as a 96-well microtiter plate.

The fixation of the antibodies or fragments thereof according to the invention to the solid matrix in a kit according to the invention may be carried out by adsorption or chemical coupling to a solid phase support. Any mean known in the art for immobilizing a protein or peptide to a solid support can be used. The antibodies or fragments thereof according to the invention can be either covalently or non-covalently bound to the solid matrix by techniques such as covalent binding via an amide or ester linkage or adsorption. Peptides can be bound using binding pairs such as biotin and avidin or antibody and antigen. After the peptides are affixed to the solid matrix, the solid matrix can be incubated with a blocking solution (containing a blocking protein such as bovine serum albumin) to reduce non-specific adsorption of antibodies in a test sample to the support surface. According to one aspect, the antibodies or fragments thereof according to the invention can be synthesized directly on the solid matrix of the kit of the invention.

According to one embodiment, when the kit comprises at least one antibody or fragment thereof according to the invention or a combination thereof for coupling to a solid matrix as solid phase support, the kit further optionally comprises coupling reagents and/or a solid matrix for performing an immunoassay.

According to another further embodiment, the kit according to the invention further comprises at least one rinsing reagent for washing unbound material before detection in order to avoid background noise detection. Typically rinsing reagents comprise standard buffers known in the art.

References cited herein are hereby incorporated by reference in their entirety. The present invention is not to be limited in scope by the specific embodiments described herein, which are intended as single illustration of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

EXAMPLES

Example 1. Generation and Isolation of the Anti-IL-15 Antibodies According to the Invention 1. Production and Sequencing of Mouse B-E29

The antibodies according to the invention derive from the commercially available mouse B-E29 antibody, also described in Bernard et al, 2004, supra, herein referred to comparative antibody 1. Briefly, mouse monoclonal antibodies, specific for human IL-15, are originally generated by immunizing BALB/c mice with recombinant human IL-15 made in *E. coli* (Peprotech 200-15). Spleens from immunized mice are fused with X6.3.AG.8653 mouse myeloma cell line and hybridoma generated using conventional techniques. Hybridoma supernatants were screened for the presence of IL-15-binding antibodies using an ELISA technique, followed by cloning dilution and isotype determination. The mouse anti-IL-15 monoclonal antibody B-E29, of IgG1 (heavy chain) κ (light chain) isotypes, was selected using this methodology, as well as other anti-IL-15 antibodies. However, when assayed for the inhibition of the proliferation of Kit 225 T cells stimulated with recombinant IL-15, only the B-E29 antibody was able to block this activity, thus B-E29 neutralizes the biological activity of IL-15 whereas other anti-IL-15 antibodies do not (data not shown).

The variable domain of the heavy chain and the variable domain of the light chain of mouse B-E29 antibody were sequenced using standard protocols. Briefly, messenger RNA (mRNA) was extracted from B-E29 hybridoma cell pellets using conventional RNA extraction and purification protocols. cDNA was created from the RNA by reverse-transcription with an oligo(dT) primer. The VH and VL regions of the monoclonal antibody DNA was amplified by PCR reactions. The VH and VL products were cloned into the Invitrogen sequencing vector pCR2.1 and transformed into TOP10 cells and screened for positive transformants by PCR. Selected colonies were picked and analyzed through sequencing. The amino acid sequence of the variable domain of the heavy chain (VH) of mouse B-E29 antibody is provided as SEQ ID NO: 32. The amino acid sequence of the variable domain of the light kappa chain (VL) of mouse B-E29 antibody is provided as SEQ ID NO: 36.

2. Humanization of Anti-IL-15 Antibodies Derived from Mouse B-E29

Using antibody-numbering systems from IMGT (international ImMunoGeneTics information system for immunoglobulins or antibodies) and Kabat, the frameworks and CDRs of the B-E29 mouse antibody were identified. Online databases of Human IgG sequences were searched for comparison to the mouse domains using BLAST search algorithms, and human variable domain frameworks selected from the top 100 BLAST results. These were reduced based on a combination of framework homology, maintaining key framework residues and canonical loop structure. Several humanized, chimeric and combinatorial antibodies were constructed, among which some had mutations on unusual residues located in the N-terminal portion of the mouse VH region, with the aim of selecting the "best" human VH and VL chains for forming antibodies retaining or increasing their binding capacity to IL-15 as well as retaining or increasing the efficiency of their production, compared to mouse B-E29 antibody (comparative antibody 1).

An alignment of the amino acid sequences of the different humanized and chimeric variants of the heavy chain variable domain of mouse B-E29 is shown in FIG. 1 (A).

An alignment of the amino acid sequences of the different humanized and chimeric variants of the light chain variable domain of mouse B-E29 is shown in FIG. 1 (B).

The VH domain of each of the above-mentioned variants was synthesized in-frame with a human IgG1 isotype constant domain (allotype Glm3) sequence of SEQ ID NO: 30.

The VL domain of each of the above-mentioned variants was synthesized in-frame with a human IgK isotype constant domain (allotype Km3) sequence of SEQ ID NO: 31.

Both the heavy chain and light chain coding sequences were cloned into the pVITRO-DHFR3 vector backbone for antibody production. Plasmids were co-transfected into suspension-adapted CHO (Chinese Hamster Ovary) cells (CHO-S cells, Invitrogen, UK). After 7 days, the culture supernatant was harvested and antibodies purified using an Amersham Biosciences AKTA Chromatography system and HiTrap Protein A column.

The combinations cVH3:cVK1 and cVH4:cVK1 did not result in sufficient antibody production to be further tested. In an ELISA assay, the combinations cVH1:cVK1, hVH1:cVK1, cVH1:hVK1 showed similar binding to human IL-15, better than that observed with hVH1:hVK2 and cVH1:hVK2 (data not shown).

These results demonstrate that among the variants tested, hVH1 and hVK1 are good candidates to form antibodies which can be efficiently produced and which bind IL-15. Therefore, they were used as starting material for further optimization.

3. Optimization of Humanized Anti-IL-15 Antibodies

Optimization consisted in changing some amino acids or amino acid motifs within the CDRs and/or frameworks of hVH1 (also called "huVH1" herewith) and hVK1 (also called "huVL1" herewith), which might lead to chemical instability or aggregation of antibodies, as well as retaining or increasing the efficiency of their production compared to mouse B-E29 antibody (comparative antibody 1). This strategy allowed the generation of variants of huVH1/huVL1 antibodies comprising the VH/VL regions indicated in above Table 1.

The VH domain of each of the variants indicated in Table 1 was synthesized in-frame with a human IgG1 isotype constant domain (allotype Glm3) sequence of SEQ ID NO: 30.

The VL domain of each of the variants indicated in Table 1 was synthesized in-frame with a human IgK isotype constant domain (allotype Km3) sequence of SEQ ID NO: 31.

Recombinant antibodies were produced in transient CHO system and further tested as culture supernatants or after purification through a protein-A FPLC column.

Example 2. Binding Potency of Various Anti-IL-15 Antibodies According to the Invention for IL-15

Some of the antibodies according to the present invention were tested for their ability to bind plate-bound recombinant human or monkey IL-15 in an ELISA assay. Fully human antibody of the prior art (146B7 described in WO 03/017935, herein referred to comparative antibody 2) was produced in the same expression system, purified and used as control.

Maxisorp plates were coated with recombinant human IL-15 (Prospec cat no. CYT230) or Rhesus macaque IL-15 (MyBiosource cat. no. MBS948894) at 100 ng/well in carbonate coating buffer for 2 hours at 37° C. Since published sequences of Rhesus macaque and Cynomolgus monkey IL-15 are identical, such recombinant IL-15 protein was referred to as Macaque Monkey IL-15. Tested human IL-15 recombinant protein has a sequence identical to that provided in SEQ ID NO: 1 but with an additional methionine at the N-terminal position as usually done for expressing recombinant proteins in *E. Coli*. Tested recombinant Macaque Monkey IL-15 was produced in yeast and has a sequence identical to that provided in SEQ ID NO: 4 but with an additional N-terminal His tag.

The plate was then blocked with 2% normal goat serum for 30 min at 37° C. and washed 6 times with PBS-Tween (0.05% Tween-20 in PBS, v/v). Test antibodies were added to the plate in triplicate at various dilutions in PBS-Tween and the plate was incubated with gentle rocking at room temperature for 2 hours. The plate was then washed 6 times with PBS-Tween and an appropriate dilution of goat anti-human IgG antibody (Millipore cat. no. AP309P) conjugated to horseradish peroxidase (HRP) was added to the plate and left rocking at room temperature for 1 hour. The plate was then washed 6 times with PBS-Tween and incubated with TMB substrate. The reaction was stopped by the addition of 1M $H_2SO_4$ and read at 450 nm. Dose response curves of absorbance versus concentration were plotted and analyzed to determine half-maximal binding concentrations ($BC_{50}$) using the Graphpad Prism software. $BC_{50}$ values expressed as molarity were extrapolated from concentration in ng/ml using a 150 kDa molecular weight value for all antibodies.

Representative $BC_{50}$ values obtained for several humanized variants of B-E29, as well as fully human 146B7 antibody used as control, are indicated in Table 2.

TABLE 2

| Antibody | Human IL-15 $BC_{50}$ (nM) | Macaque Monkey IL-15 $BC_{50}$ (nM) |
| --- | --- | --- |
| 146B7 (comparative antibody 2) | 8.407 | 0.733 |
| huB-E29-1 | 1.333 | 0.487 |
| huB-E29-2 | 1.467 | 0.340 |
| huB-E29-3 | 2.620 | NT |
| huB-E29-4 | 1.013 | 0.500 |
| huB-E29-5 | 1.473 | 0.453 |
| huB-E29-6 | 1.840 | NT |
| huB-E29-7 | 0.840 | 0.433 |
| huB-E29-8 | 1.787 | NT |
| huB-E29-9 | 1.987 | NT |
| huB-E29-10 | 0.507 | 0.353 |
| huB-E29-11 | 0.980 | NT |
| huB-E29-12 | 0.593 | NT |
| huB-E29-13 | 3.173 | NT |
| huB-E29-14 | 0.813 | 0.347 |
| huB-E29-15 | 2.533 | NT |
| huB-E29-16 | 2.007 | NT |
| huB-E29-17 | 2.613 | NT |
| huB-E29-18 | 0.693 | 0.367 |
| huB-E29-19 | 2.207 | NT |
| huB-E29-22 | 3.867 | NT |
| huB-E29-24 | 0.647 | 0.113 |
| huB-E29-30 | 5.867 | NT |
| huB-E29-31 | 3.514 | NT |
| huB-E29-34 | 3.887 | NT |

NT: not tested

As shown in Table 2, while some antibody variants according to the invention had a binding activity comparable to each other, others showed improved binding to human IL-15 (e.g. huB-E29-10 and huB-E29-24). FIG. 2A shows that a representative humanized B-E29 variant (huB-E29-1) displays not only better potency in binding to human IL-15 than the 146B7 antibody, but also a higher maximal signal suggesting that the efficacy at binding IL-15 is improved. This improved capacity to bind human IL-15 is further confirmed in example 3, Table 3.

In the cases where binding to Macaque Monkey IL-15 was tested, all antibody variants according to the invention which bind to human IL-15 also bind to Macaque Monkey IL-15, with slightly higher potencies.

Example 3. Binding Kinetics and Affinity for Human IL-15 with Some of the Anti-IL-15 Antibodies According to the Invention The association rate ($k_a$), dissociation rate ($k_d$) and equilibrium dissociation constant ($K_D$) of three humanized B-E29 antibody variants according to the invention towards recombinant human IL-15 were determined by surface plasmon resonance (SPR).

Human IL-15 (Prospec cat no. CYT230) was immobilized onto a CM5 chip (GE Healthcare) using standard amine coupling, and antibodies injected at various concentrations in 120 µl phosphate buffer saline with a flow rate of 40 µl/ml. Binding kinetics were analyzed on a Biacore 3000 apparatus (GE Healthcare) with a 300 seconds dissociation period. Reference signal and 0 nM antibody concentration signal were substracted and data fitted using a 1:1 (Langmuir) binding model.

TABLE 3

| Antibody | $k_a$ ($M^{-1} \cdot s^{-1}$) | $k_d$ ($s^{-1}$) | $K_D$ (pM) | Rmax (RU) |
| --- | --- | --- | --- | --- |
| huB-E29-2 | $1.15 \times 10^6$ | $1.07 \times 10^{-5}$ | 9.4 | 214 |
| huB-E29-10 | $1.43 \times 10^6$ | $4.23 \times 10^{-4}$ | 295 | 212 |
| huB-E29-24 | $1.75 \times 10^6$ | $5.74 \times 10^{-4}$ | 329 | 167 |
| 146B7 (comparative antibody 2) | $1.44 \times 10^6$ | $5.26 \times 10^{-5}$ | 36.7 | 57.3 |

RU: Relative units

While the on-rate ($k_a$, association rate) of all compared humanized B-E29 antibodies was similar, the off-rate ($k_d$, dissociation rate) of huB-E29-2 was slower, resulting in a lower equilibrium dissociation constant $K_D$ (Table 3). The 146B7 antibody also showed a low $K_D$, similar to what reported (Villadsen, et al, 2003, *J. Clin. Invest.* 112:1571-1580). However, the maximal (Rmax) signal given by the association of 146B7 on human IL-15 coated chip was much lower than that observed with the three humanized B-E29 antibody variants. This result is similar to what was observed by ELISA in example 2 and suggests that these three humanized B-E29 antibody variants have improved binding capacity to human IL-15, compared to the 146B7 antibody.

Example 4. Species-Specificity of Some Anti-IL-15 Antibodies According to the Invention Antibodies according to the present invention were tested for their ability to bind plate-bound recombinant mouse or rat IL-15 in an ELISA assay.

Maxisorp plates were coated with recombinant mouse IL-15 (R&D Systems cat. no. 447-ML) or rat IL-15 (Sigma cat. no. SRP4172) at 100 ng/well in carbonate coating buffer for 2 hours at 37° C. Tested IL-15 recombinant proteins have a sequence identical to that provided in SEQ ID NO: 2 (mouse IL-15) and SEQ ID NO: 3 (rat IL-15) but with an additional methionine at the N-terminal position as usually done for expressing recombinant proteins in *E. Coli*.

The plate was then blocked with 2% normal goat serum for 30 min at 37° C. and washed 6 times with PBS-Tween (0.05% Tween-20 in PBS, v/v). Test antibodies were added to the plate in triplicate at various dilutions in PBS-Tween and the plate was incubated with gentle rocking at room temperature for 2 hours. As positive controls, rabbit-anti-mouse IL-15 (Acris cat. no. AP01124PU-S) or rabbit anti-rat IL-15 (Biovision cat. no. 5172) antibodies were tested at the same concentrations. The plate was then washed 6 times with PBS-Tween and an appropriate dilution of HRP-conjugated goat anti-human IgG antibody (Millipore cat. no. AP309P) for humanized antibodies, or goat-anti-rabbit IgG antibody (Sigma cat. no. A 4416) for the positive controls was added and the plate was left rocking at room temperature for 1 hour. The plate was then washed 6 times with PBS-Tween and incubated with TMB substrate. The reaction was stopped by the addition of 1M $H_2SO_4$ and read at 450 nm. Dose response curves of absorbance versus concentration were plotted using the Graphpad Prism software.

As shown in FIG. 2B and FIG. 2C, none of the tested humanized variants of B-E29 showed significant binding, at the concentrations tested, to mouse or rat IL-15, while good binding was observed with the positive controls.

Example 5. Selectivity of Some Anti-IL-15 Antibodies According to the Invention Since IL-2 is the cytokine closest to IL-15 by sequence homology, and IL-2 and IL-15 share two common receptor chains (the IL-2/IL-15Rβ chain and the common γc chain), the binding of anti-IL-15 antibodies of the present invention to IL-2 was assessed by ELISA.

Maxisorp plates were coated with recombinant human IL-2 (R&D Systems cat. no. 202-IL-010) of SEQ ID NO: 38 at 100 ng/well in carbonate coating buffer for 2 hours at 37° C. The plate was then blocked with 2% normal goat serum for 30 min at 37° C. and washed 4 times with PBS-Tween (0.05% Tween-20 in PBS, v/v). Test antibodies or positive control biotinylated antibody (anti-IL-2 Novus Bio cat. no. NBP1-43491) were added to the plate in duplicate at 5 µg/ml in PBS-Tween and the plate was incubated with gentle rocking at room temperature for 2 hours. The plate was then washed 4 times with PBS-Tween and an appropriate dilution of goat anti-human IgG antibody (Millipore cat. no. AP309P) conjugated to horseradish peroxidase (HRP) for test antibodies, or streptavidin-HRP for positive control antibody, was added to the plate and left rocking at room temperature for 1 hour. The plate was then washed 4 times with PBS-Tween and incubated with TMB (3,3',5,5'-tetramethylbenzidine) substrate. The reaction was stopped by the addition of 1 M $H_2SO_4$ and read at 450 nm.

Figure 3:
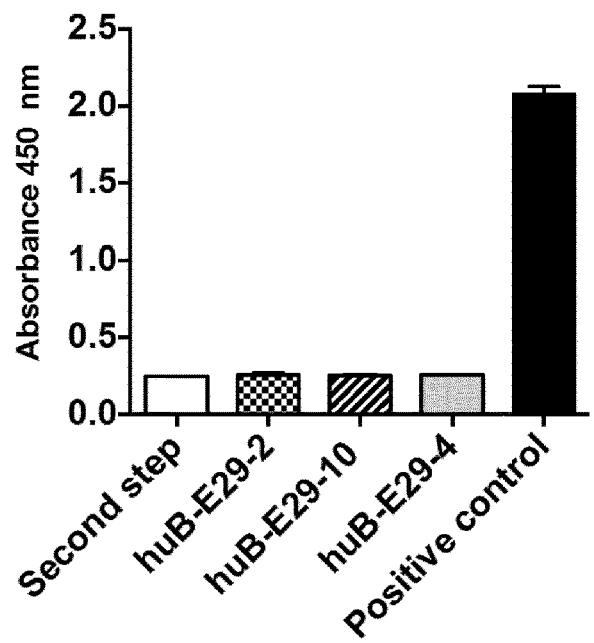
FIG. 3. Binding of anti-IL-15 antibodies to recombinant human IL-2 as determined by ELISA. Bars represent the average duplicate values of absorbance at 450 nm for a fixed 5 µg/ml concentration of test anti-IL-15 antibodies or positive control anti-IL-2 antibody. Second step alone is HRP-anti-human immunoglobulin in absence of test antibody.

FIG. 3 shows that none of the tested anti-IL-15 antibodies according to the invention binds human IL-2 at the 5 µg/ml concentration tested, whereas a positive control antibody showed strong binding.

Example 6. Inhibition of Soluble IL-15-Induced Proliferation/Survival in Cell Lines by Some Anti-IL-15 Antibodies According to the Invention Antibodies according to the present invention were tested for their ability to inhibit IL-15-induced Kit 225 or M-07e cell proliferation/survival (Finch et al, 2011, supra).

The Kit 225 cell line was established from a patient with T cell chronic lymphocytic leukemia (Hori et al., 1987, *Blood*, 70:1069-1072). Kit 225 cells express the 3 chains of the IL-15 receptor (IL-15Rα, IL-15Rβ and IL-15Rγ) (Mortier et al., 2006, *J. Biol. Chem.*, 281:1612-1619). The M-07e cell line was established from the peripheral blood of a 6-month-old girl with acute megakaryoblastic leukemia (Brizzi et al., 1990, *Br J Haematol.*, 76:203-239). M-07e cells express only the IL-15Rβ and IL-15Rγ chains of the IL-15 receptor (Meazza et al., 1998, *Int. J. Cancer*, 78:189-95).

Kit 225 cells (Hori et al., 1987, *Blood*, 70(4):1069-1072) and M-07e cells (Leibniz-Institute DSMZ) were grown and maintained in RPMI 1640 medium supplemented with 10 mM Hepes, 100 IU/ml penicillin, 100 µg/ml streptomycin, 2 mM L-Glutamine, 1 mM sodium pyruvate, 10% heat-inactivated Fetal Bovine Serum (FBS, PAA) and 200 U/ml human IL-2 (R&D Systems cat. no. 202-IL) of SEQ ID NO: 38. One day prior the experiments, cells were starved in the same culture medium without IL-2 for 24 hours. After that, $5 \times 10^4$ cells were added per well in 96-well plates in triplicate, in the presence of various dilutions of test antibodies as wells as recombinant human IL-15 (R&D systems cat. no. 247-IL) or recombinant monkey IL-15 (My Biosource cat. no. MBS948894) at 1 ng/ml final concentration and a total volume of 100 µl culture medium per well. As mentioned above, because published sequences of Rhesus macaque and cynomolgus macaque IL-15 are identical, such recombinant IL-15 protein was referred as to Macaque Monkey IL-15.

Cell cultures were maintained for 48 h at 37° C., under 5% $CO_2$ and then 100 µl of Titerglo solution (which measures ATP consumption, Promega) were dispensed to each well and contents mixed by vigorous pipetting. Plates were incubated for 15-20 min at room temperature before reading. Luminescence signal was read in a plate reader as a measure of cell survival. Using Graphpad Prism software, corrected values against antibody concentrations were plotted and half-maximum inhibitory concentrations ($IC_{50}$) determined using log inhibitor versus response (three parameters). $IC_{50}$ values expressed as molarity were extrapolated from concentration in ng/ml using a 150 kDa molecular weight value for all antibodies.

TABLE 4

| Antibody | IC$_{50}$ in M-07e cells (nM) | | IC$_{50}$ in Kit 225 cells (nM) | |
|---|---|---|---|---|
| | Human IL-15 | Macaque Monkey IL-15 | Human IL-15 | Macaque Monkey IL-15 |
| huB-E29-2 | 0.017 | 0.23 | 0.083 | 0.112 |
| huB-E29-10 | 4.2 | 41.3 | 17.0 | 17.5 |
| huB-E29-24 | 19.1 | 10.4 | 29.3 | 26.7 |
| 146B7 comparative antibody 2 | 3.2 | NT | 3.7 | NT |

NT: not tested

As shown in Table 4, the three humanized B-E29 antibody variants tested as wells as 146B7 were able to inhibit IL-15-induced proliferation/survival of M-07e and Kit 225 cells. The humanized huB-E29-2 was superior in potency to all the other tested antibodies in M-07e cells, as well as in Kit 225 cells.

Example 7. Inhibition of Trans IL-15-Induced Proliferation/Survival in Cell Line by Some Anti-IL-15 Antibodies According to the Invention Some antibodies according to the present invention were tested for their ability to inhibit human IL-15-induced M-07e cell (expressing only IL-15Rβγ) proliferation/survival, with IL-15 being presented after binding to a IL-15Rα-Fc construct immobilized on plastic. This experimental set-up mimics the trans presentation of IL-15 described in the literature and seemingly important for the biology of IL-15 (Stonier, et al, 2010, supra).

Wells from 96-well plates were coated with 1 μg recombinant human IL-15Rα-Fc chimera (R&D Systems cat. No 7194-IR-050) in 100 μl PBS for 2 hours at 37° C. Contents of wells were aspirated, then 150 μl of RPMI 1640 medium supplemented with 10 mM Hepes, 100 IU/ml penicillin, 100 μg/ml streptomycin, 2 mM L-Glutamine, 1 mM sodium pyruvate, 10% heat-inactivated Fetal Bovine Serum (FBS, PAA), referred as culture medium, were added per well and plates were incubated for 30 min at 37° C. Contents of wells were aspirated, then 100 μl of a 300 ng/ml solution of human IL-15 (R&D Systems) was added and plates were incubated for 1 hour at 37° C. Contents of wells were aspirated, then 200 μl of culture medium was used twice to wash unbound IL-15. Various concentrations of test antibodies were added to each well in triplicate, then 5×10$^4$ M-07e cells (left overnight in medium without cytokine) were added. Control wells were adequately designed to make sure that IL-15 did not induce proliferation/survival in this system in absence of IL-15Rα-Fc, and that IL-15Rα-Fc did not induce proliferation/survival in absence of IL-15.

Cell cultures were maintained for 48 h at 37° C., under 5% CO2 and then 100 μl of Titerglo solution (which measures ATP consumption, Promega) are dispensed to each well and contents mixed by vigorous pipetting. Plates were incubated for 15-20 min at room temperature before reading. Luminescence signal was read in a plate reader as a measure of cell survival. Using Graphpad Prism software, corrected values against antibody concentrations were plotted and half-maximum inhibitory concentrations (IC$_{50}$) were determined using log inhibitor versus response (three parameters). IC$_{50}$ values expressed as molarity were extrapolated from concentration in ng/ml using a 150 kDa molecular weight value for all antibodies.

TABLE 5

| Antibody | IC$_{50}$ in M07e cells for IL-15 trans presentation (nM) |
|---|---|
| huB-E29-2 | 0.37 |
| huB-E29-10 | 0.53 |
| huB-E29-24 | 0.65 |
| 146B7 comparative antibody 2 | 0.63 |

As shown in Table 5, all tested humanized B-E29 antibody variants inhibited trans presentation of human IL-15 to M-07e cells with similar potency.

Example 8: Absence of Interference with the Binding of Human IL-15 to IL-15Rα of Some Anti-IL-15 Antibodies According to the Invention Antibodies according to the present invention were tested for their ability to inhibit binding of biotinylated human IL-15 to a plate-bound IL-15-Rα-Fc recombinant construct (R&D Systems) according to the method described by Finch et al. (Finch et al, 2011, supra).

Interleukin-15Rα-Fc in phosphate-buffered saline (PBS) at a concentration of 600 pM was coated onto MaxiSorp 96-well plates by incubation at 4° C. for 16 h. The wells were washed with PBS and blocked with PBS containing 3% (w/v) bovine serum albumin (BSA) for 2 h and washed again with PBS. Antibodies and controls (including an antibody known to block IL-15 binding to IL-15Rα, R&D Systems cat. no. NF150) were diluted in PBS with 0.1% (w/v) BSA and added to the IL-15Rα-Fc coated assay wells. Biotinylated human IL-15 (R&D Systems cat. no. NF150) at a final concentration of 100 pM was added and the assay plates incubated for 1 h. The plates were then washed three times with PBS containing 0.1% (v/v) Tween 20 followed by addition of an optimal dilution of streptavidin-peroxidase. After 30 min incubation the plates were washed seven times with PBS containing 0.1% (v/v) Tween 20 and peroxidase substrate added. Once the reaction completed and stopped with $H_2SO_4$, absorbance was measured at 450 nm emission wavelength.

Figure 4:
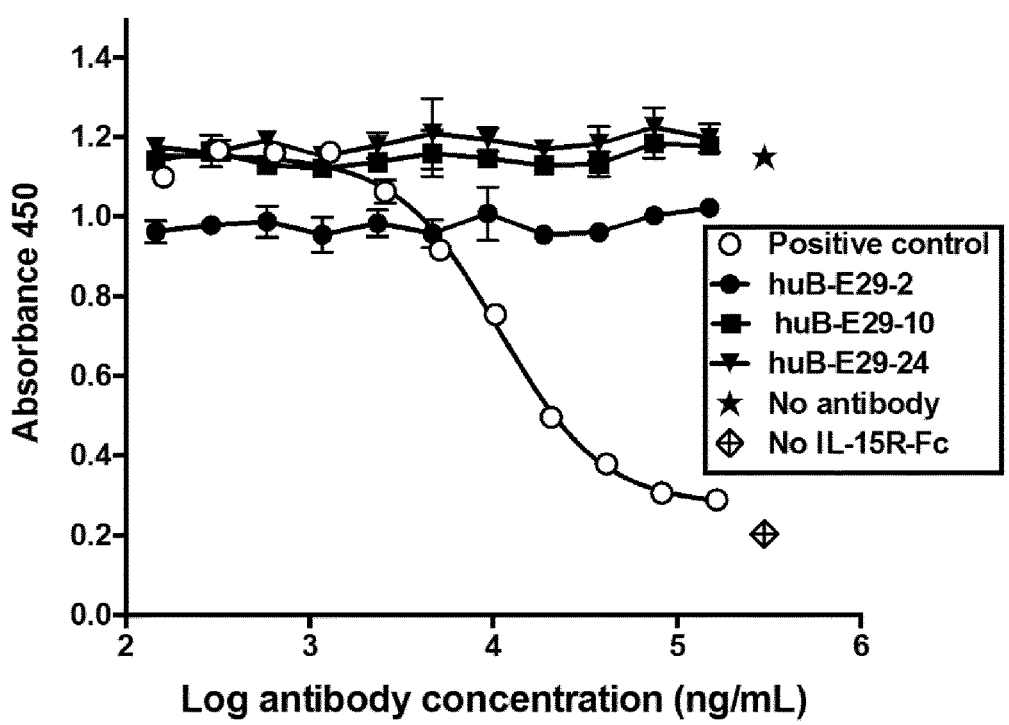
FIG. 4. Dose response-curves of the binding of biotinylated human IL-15 to IL-15Rα-Fc in the presence of various concentrations of antibodies as determined by ELISA, expressed as absorbance at 450 nm. Binding of three exemplary anti-IL-15 antibodies of the invention are shown compared to that of a control antibody known to block IL-15 binding to IL-15Rα, and to the binding of biotinylated IL-15 in absence of antibody or in absence of IL-15Rα-Fc.

FIG. 4 shows that a positive control antibody was able to inhibit in a dose-dependent manner binding of biotinylated human IL-15 to IL-15-Rα-Fc while the anti-IL-15 antibodies huB-E29-2, huB-E29-10 and huB-E29-24 were not, up to the highest tested dose of 150 μg/ml. In contrast, based on the observations by Bernard et al., 2004 supra, monoclonal mouse anti-IL-15 antibody B-E29 (comparative antibody 1) prevents IL-15 binding to IL-15Rα.

Example 9: In Vivo Neutralization of Human IL-15 of Some Anti-IL-15 Antibodies According to the Invention Mouse cells are responsive to human IL-15, which allows testing in vivo functional inhibition of IL-15 of anti-IL-15 antibodies according to the invention even though those antibodies do not recognize mouse IL-15 as shown in Example 4. Interleukin-15 injected into mice can induce proliferation and accumulation of various lymphocyte subsets such as Natural Killer (NK) cells in the spleen. However, IL-15 by itself is poorly active, may be due to its very short half-life, and stabilized complexes of IL-15 bound to IL-15Rα are more efficient in vivo.

Exemplary antibodies of the present invention were tested for their capacity to inhibit IL-15/IL-15Rα-Fc complex-induced NK cell accumulation in the spleen of C57BL/6 male mice (Finch et al, 2011, supra). Groups of 5 mice were injected during three consecutive days with a mixture of 1 µg human IL-15 (Prospec) and 3.6 µg human IL-15Rα-Fc (R&D Systems) and on the first and second days of the experiment with 100 µg and 62 µg, respectively, of test antibodies and controls. One day after the last injection, spleens were harvested, splenocytes counted and NK cells analysed by flow cytometry and defined as CD45+NK1.1+ CD3− cells.

Figure 5:
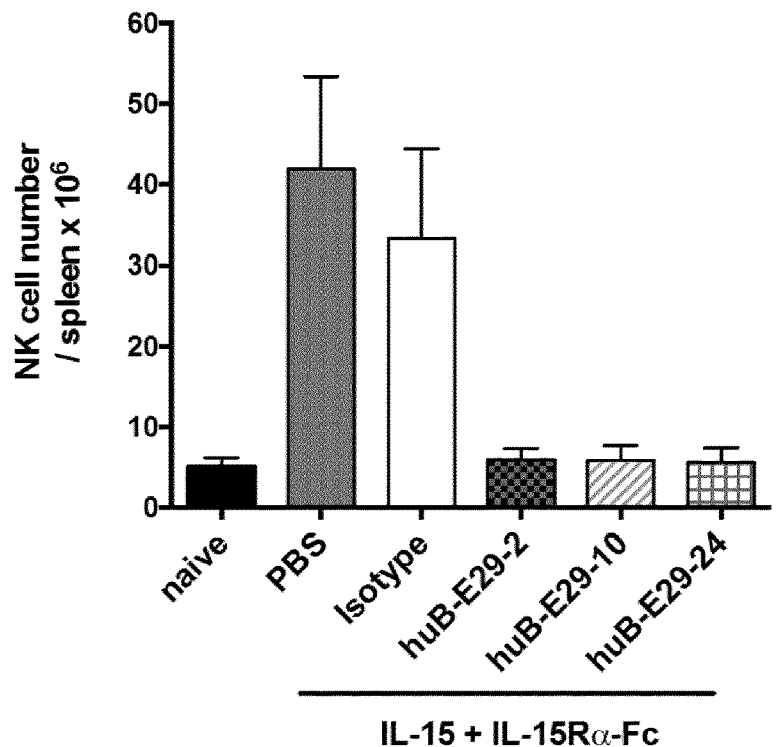
FIG. 5. Enumeration of NK cells in the spleen of mice injected with vehicle (naïve), or with IL-15/IL-15Rα-Fc complex followed by exemplary anti-IL-15 antibodies or a control human IgG1 isotype. Results are expressed as mean±standard deviation of 5 animals per group.

As shown in FIG. 5, injection of the IL-15/IL-15Rα-Fc complex induced robust NK cell accumulation in mouse spleen that could be fully inhibited by treatment with the exemplary huB-E29-2, huB-E29-10 and huB-E29-24 antibodies of the invention but not a control human IgG1 isotype antibody.

Example 10: Epitope Mapping of Anti-IL-15 Antibodies According to the Invention

Epitope mapping of anti-IL-15 antibodies of the invention was performed by analysing the binding of said antibodies to libraries of structured peptides designed to represent linear but also discontinuous epitopes of IL-15 by using the Chemically Linked Peptides on Scaffolds (CLIPS) technology (Pepscan Presto By, Lelystad, The Netherlands). CLIPS technology (Timmermann et al., 2007, *J. Mol. Recognit.*, 20, 283-99) allows to structure peptides into single loops, double loops, triple loops, sheet-like folds, helix-like folds, and combinations thereof. Structure peptides are immobilized on arrays. The binding of antibodies to each of the synthesized peptides was tested in a PEPSCAN-based array ELISA. Signal for each peptide is measured using a charge coupled device camera, quantified and results from the whole array processed to define which peptides are best recognized. Amino-acid substitutions within peptides can allow determining more critical binding residues.

It was found using this technique that the antibodies of the invention huB-E29-2, huB-E29-10 and huB-E29-24 all preferentially bind to linear and constrained peptides containing the peptide stretch of sequence $^{61}$DTVENLIILANN$^{72}$ (SEQ ID NO: 43) This observation is similar to what reported for comparative antibody 1, B-E29 (Bernard et al., 2004, supra). Using single amino-acid substitution, residues found to be most essential for the binding of the antibodies of the invention huB-E29-2, huB-E29-10 and huB-E29-24 antibodies to IL-15 were D61, E64, I68 and N71.

Comparative antibody 1, is characterised by VL and VH as shown in SEQ ID NO: 39 SEQ ID NO: 40 respectively. According to Bernard et al., 2004, supra, B-E29 affects binding of IL-15 to IL-15Rα through binding to L66 and I67 residues, which are not found as critical for the binding of the antibodies of the invention huB-E29-2, huB-E29-10 and huB-E29-24. On the other hand, still according to Bernard et al., residues E64, N65 and I68 are important for prevention of binding of IL-15 to IL-15Rβ by B-E29, and two of these three residues, E64 and I68, were found critical for the huB-E29-2, huB-E29-10 and huB-E29-24 antibody binding to IL-15. Prevention of binding of IL-15 to the IL-15Rβ chain is important to block IL-15 signalling. Therefore, although the huB-E29-2, huB-E29-10 and huB-E29-24 antibodies share an overlapping epitope with the original B-E29 antibody, structural differences may explain a different mode of action, which is the loss of ability to prevent IL-15 binding to IL-15Rα, as shown in the present application (Example 8), while preserving the ability to block IL-15 mediated signalling.

It was also observed that the antibodies of the invention huB-E29-10 and huB-E29-24 showed less tolerance for substitutions within the peptide stretch of SEQ ID NO: 43 than the huB-E29-2 antibody, meaning that loss of signal was more frequent, which could be related to their lower affinity for IL-15 as shown in the present application (Example 3).

Finally, comparative antibody 2, 146B7, did not show any reliable binding over background on any of the peptide arrays tested and therefore probably recognizes a complex/discontinuous epitope on IL-15 (Villadsen et al., 2003, *J. Clin. Invest.*, 112: 1571-1580). Amino acid mutagenesis, reported that residues D8 and Q108 of IL-15 were essential for the binding of 146B7, without further description of the epitope recognized by this antibody. Data presented in the current example are in accordance with this finding, suggesting a non-linear epitope for 146B7, clearly distinct from the ones recognized by the antibodies of the invention huB-E29-2, huB-E29-10 and huB-E29-24.

The epitope recognized by the DISC0280 anti-IL-15 antibody (comparative antibody 3) was determined using crystallography (Lowe et al, 2010, *J. Mol. Biol.*, 406, p. 160-175). DISC0280 antibody is characterised by VL CDR3 and VH CDR3 as shown in SEQ ID NO: 41 and SEQ ID NO: 42 respectively. As expected from the fact that comparative antibodies B-E29 and DISC0280 competed for IL-15 binding (Finch et al, 2010, *J Mol Biol.*, 406(1), p. 160-175), similar residues were found between the DISC0280 epitope and the epitopes recognized by the huB-E29-2, huB-E29-10 and huB-E29-24 antibodies of the present invention, namely E64 and N71. However, other hydrogen bonds were described for DISC0280 with IL-15 residues: K41, E46, Q48, L52, E53, and E89. Hence, DISC0280 and the antibodies of the invention huB-E29-2, huB-E29-10 and huB-E29-24 have an overlapping but distinct epitope. In addition, two residues found most important for the binding of huB-E29-2, huB-E29-10 and huB-E29-24 to IL-15 are not part of DISC0280 epitope: D61 and I68.

Example 11: Effect of Anti-IL-15 Antibodies According to the Invention in Cell Lines from Refractory Celiac Disease Patients The effects of the antibody of the invention huB-E29-2 and comparative antibody 146B7 on the prevention from apoptosis and activation of type II refractory celiac disease (RCD) patient primary intra epithelial lymphocytes (IEL) cell lines induced by recombinant human IL-15, were assessed in vitro. The percentage of apoptotic cells was analysed by staining cells with Annexin V and propidium iodide (PI) and measured by flow cytometry. The expression of phosphorylated STAT5 protein (pSTAT5), also by a flow cytometry technique, was used to measure activation of the primary IEL cell lines by IL-15 and its inhibition by anti-IL-15 antibodies.

Figure 6:
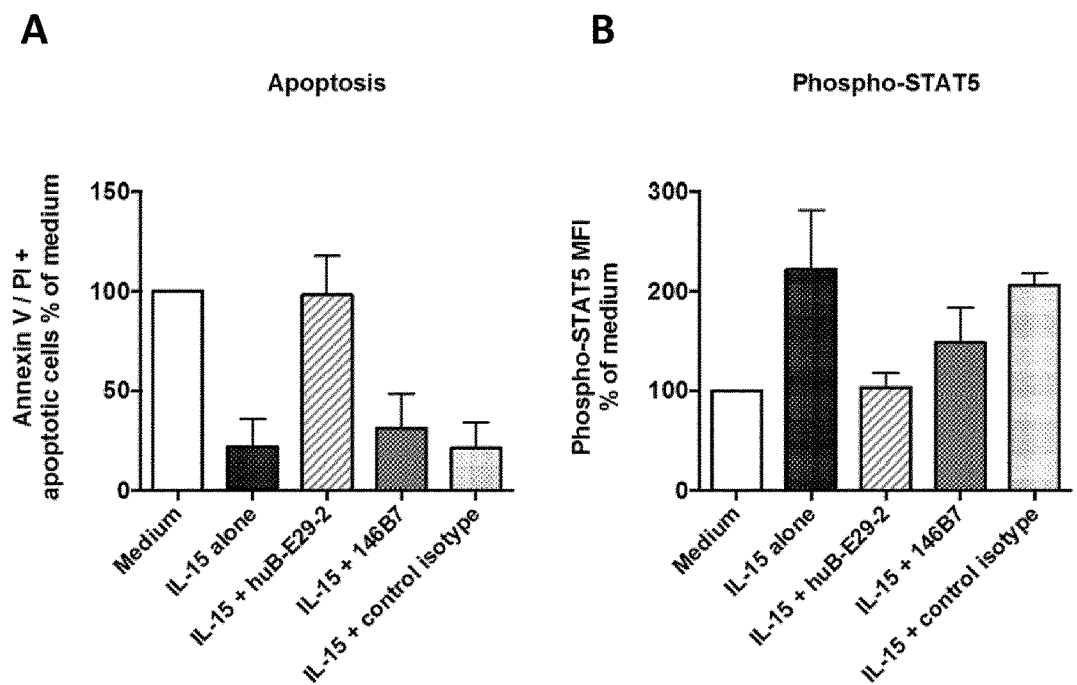
FIG. 6. Effects of huB-E29-2, 146B7 and control isotype antibodies on IL-15-induced prevention of apoptosis and STAT5 phosphorylation in three type II RCD primary cell lines. Results were normalized to levels in control condition (medium, set at 100%) for the percentage of apoptotic cells (A) or the MFI of phosphorylated STAT5 intracellular expression (B) induced by IL-15, and expressed as mean plus standard deviation (SD) of results obtained with type II RCD IEL cell lines from three different patients.

The humanized anti-IL-15 antibody of the invention huB-E29-2 potently inhibited IL-15-induced prevention of apoptosis in type II RCD primary IEL cell lines from three different patients in vitro (FIG. 6), with a half-maximal inhibitory concentration (IC$_{50}$) of 2.36 nM calculated for one of the three cell lines tested (HAM RAC). This antibody also inhibited IL-15-induced STAT5 phosphorylation in all tested type II RCD patient primary IEL cell lines, when used at the concentration calculated to give 80% apoptosis inhibition in the HAM RAC cell line. Finally, at this same concentration, huB-E29-2 was much more efficient than the fully human anti-IL-15 antibody 146B7 for the inhibition of IL-15-induced prevention of apoptosis and STAT5 phosphorylation in type II RCD patient primary IEL cell lines (FIG. 6).

Example 12: Effects of Anti-IL-15 Antibodies According to the Invention in Mice Transgenic for Human IL-15, a Model for Refractory Celiac Disease Transgenic mice overexpressing human IL-15 under the control of T3b, an enterocyte-specific promoter (IL-15TgE mice; Ohta et al., 2002, *J. Immunol.* 169(1), 460-468) show an abnormal and massive accumulation of intra-epithelial lymphocytes (IEL). This model has been postulated to recapitulate some of the features of human refractory celiac disease (Malamut et al., 2010, supra). An antibody against IL-15, AMG 714, with an identical sequence as the 146B7 antibody described herein and formerly identified as HuMaxIL-15 (Villadsen at al., 2003, *J Clin Invest,* 112(10): 1571-80; Lebrec et al, 2013, *J Immunol.,* 191(11):5551-8), is able to reverse the accumulation of IELs when administered to these mice, by promoting IEL apoptosis (Malamut et al., 2010, supra).

Figure 7:
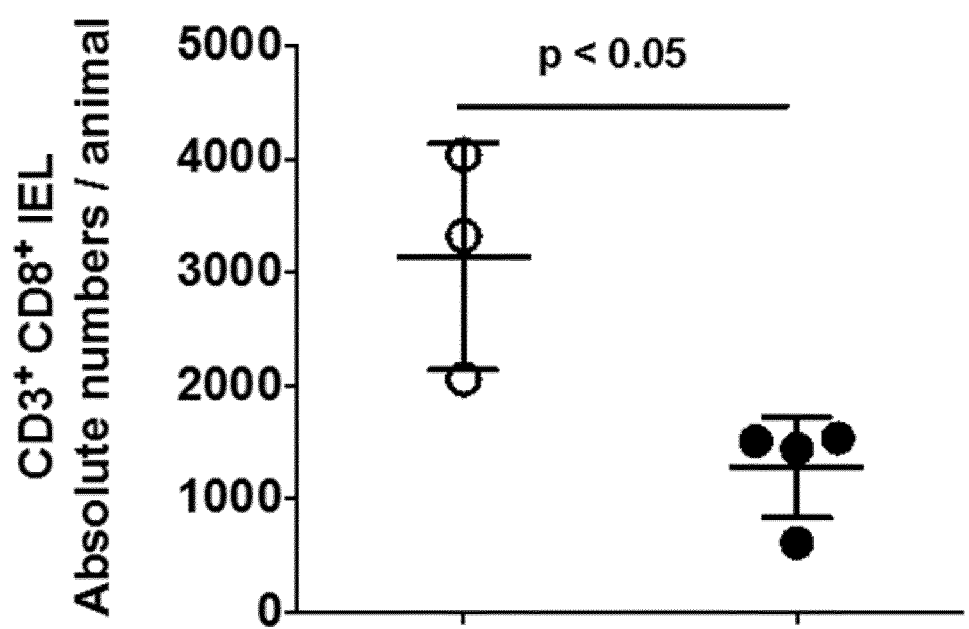
FIG. 7. Enumeration of CD3$^+$CD8$^+$ intraepithelial lymphocytes (IEL) in T3b-hIL-15 transgenic mice treated for two weeks with two weekly intraperitoneal injections of 100 µg huB-E29-2 (filled circles) or control isotype antibodies (empty circles). Each symbol represents an individual mouse, and group mean plus standard deviation (SD) are plotted. Statistical analysis: unpaired Student's t test.

The anti-IL-15 antibody of the invention huB-E29-2, or a control isotype antibody IgG1, was administered intraperitoneally twice a week at a dose of 100 μg to groups of T3b-hIL-15 transgenic mice. After the two-week treatment, CD3$^+$CD8$^+$ IEL were numerated and analysed using standard flow cytometry techniques (Malamut et al., 2010, supra). It was observed that the huB-E29-2 treatment resulted in a statistically significant decrease of CD3$^+$CD8$^+$ IEL when compared to the control antibody (FIG. 7).

Example 13: Effects of Anti-IL-15 Antibodies in an Allergen-Induced Model of Eosinophilic Esophagitis Mice genetically deficient for the IL-15Rα chain of the IL-15 receptor were resistant to induction of eosinophilic esophagitis following nostril instillation of *Aspergillus fumigatus* (Zhu et al, 2010, supra). Antibodies that bind and neutralize mouse IL-15 such as clone AIO.3 (eBiosciences) are administered to mice challenged with *Aspergillus fumigatus* to test the activity of anti-IL-15 antibodies for the treatment of eosinophilic esophagitis. Groups of mice are administered intra-nasally with a preparation of *Aspergillus fumigatus* on study days 0, 2, 4, 7, 9, 11, 14, 16, and 18. Animals are treated at different time points with appropriate doses of a neutralizing anti-mouse IL-15 antibody or control isotype antibody. As positive control, mice are treated with dexamethasone. On study Day 19, the esophagus of each mouse is processed and stained and eosinophilic infiltrate is measured via a microscope. In addition, bronchoalveolar lavage is performed to measure the infiltration of inflammatory cells in the airways.

Example 14: Effect of Anti-IL-15 Antibodies According to the Invention on Circulating NK Cell Numbers in Non-Human Primates Administration of anti-IL-15 antibodies to cynomolgus monkeys was shown to induce a decrease of circulating NK cell numbers within a two-week period (Lebrec et al., 2013, *J Immunol,* 191(11), 5551-5558). Different antibodies showed different effect: the minimal dose of anti-IL-15 Hu714MuXHu antibody able to induce NK cell reduction in vivo was 0.1 mg/kg, whereas the minimal dose of anti-IL-15 AMG 714 antibody, with an identical sequence as the 146B7 antibody described herein (Villadsen at al., 2003, *J Clin Invest,* 112(10): 1571-80; Lebrec et al, 2013, *J Immunol,* 191(11):5551-8), able to induce NK cell reduction in vivo was 150 mg/kg.

The capacity of anti-IL-15 antibodies of the invention to modulate circulating NK cell numbers is tested in vivo in cynomolgus monkeys. Various doses of said antibodies, ranging from 0.1 mg/kg to 10 mg/kg, are administered to cynomolgus monkeys via intravenous route, and circulating numbers of NK cells are evaluated using a flow cytometry technique applied to blood samples pre-dose and at study days 1, 3, 5, 8, 14, and 21. The modulation of circulating NK cell numbers in non-human primates could define a marker of the pharmacological activities of anti-IL-15 antibodies in vivo, and therefore could be advantageously used to define optimal dosing in patients

---

LIST OF SEQUENCES

```
Human mature IL-15
SEQ ID NO: 1
NWVNVISDLKKIEDLIQSMHIDATLYTESDVHPSCKVTAMKCFLLELQVISLESGDAS
IHDTVENLIILANNSLSSNGNVTESGCKECEELEEKNIKEFLQSFVHIVQMFINTS Mouse mature IL-15
SEQ ID NO: 2
NWIDVRYDLEKIESLIQSIHIDTTLYTDSDFHPSCKVTAMNCFLLELQVILHEYSNMT
LNETVRNVLYLANSTLSSNKNVAESGCKECEELEEKTFTEFLQSFIRIVQMFINTS Rat mature IL-15
SEQ ID NO: 3
NWIDVRYDLEKIESLIQFIHIDTTLYTDSDFHPSCKVTAMNCFLLELQVILHEYSNMT
LNETVRNVLYLANSTLSSNKNVIESGCKECEELEERNFTEFLQSFIHIVQMFINTS Rhesus macaque/Cynomolgus monkey mature IL-15
SEQ ID NO: 4
NWVNVISDLKKIEDLIQSMHIDATLYTESDVHPSCKVTAMKCFLLELQVISHESGDTD
IHDTVENLIILANNILSSNGNITESGCKECEELEEKNIKEFLQSFVHIVQMFINTS huVH1
SEQ ID NO: 5
EVRLMASGGGLVQPGGSLRLSCAASEFTFSNYAMSWVRQAPGKGLEWVATISRGGDYT
YYPDSVKGRFTISRDNSKNTLYLQMNSLRAEDTAVYYCARRVSMITGGWAMDYWGQGT
LVTVSS
```

LIST OF SEQUENCES huVH2
SEQ ID NO: 6
EVQLVESGGGLVQPGGSLRLSCAAS<u>EFTFSNYAMS</u>WVRQAPGKGLEWVA<u>TISRGGDYT
YYPDSVKG</u>RFTISRDNSKNTLYLQMNSLRAEDTAVYYC<u>ARRVSMITGGWAMDY</u>WGQGT
LVTVSS huVH3
SEQ ID NO: 7
EVRLMASGGGLVQPGGSLRLSCAAS<u>EFTFSNYAMS</u>WVRQAPGKGLEWVS<u>TISRGGDYT
YYPDSVKG</u>RFTISRDNSKNTLYLQMNSLRAEDTAVYYC<u>ARRVSMITGGWAMDY</u>WGQGT
LVTVSS huVH4
SEQ ID NO: 8
EVRLMASGGGLVQPGGSLRLSCAAS<u>EFTFSNYAMS</u>WVRQAPGKGLEWVA<u>TISRGGDYT
YYPDSVKG</u>RFTISRDNSKNTLYLQMNSLRAEDTAVYYC<u>ARRVSLITGGWAMDY</u>WGQGT
LVTVSS huVH5
SEQ ID NO: 9
EVRLMASGGGLVQPGGSLRLSCAAS<u>EFTFSNYAMS</u>WVRQAPGKGLEWVA<u>TISRGGDYT
YYPESVKG</u>RFTISRDNSKNTLYLQMNSLRAEDTAVYYC<u>ARRVSFITGGWAMDY</u>WGQGT
LVTVSS huVH6
SEQ ID NO: 10
EVRLMASGGGLVQPGGSLRLSCAAS<u>EFTFSNYAMS</u>WVRQAPGKGLEWVA<u>TISRGGDYT
YYPDTVKG</u>RFTISRDNSKNTLYLQMNSLRAEDTAVYYC<u>ARRVSIITGGWAMDY</u>WGQGT
LVTVSS huVH7
SEQ ID NO: 11
EVRLMASGGGLVQPGGSLRLSCAAS<u>EFTFSNYAMS</u>WVRQAPGKGLEWVA<u>TISRGGDYT
YYPDTVKG</u>RFTISRDNSKNTLYLQMNSLRAEDTAVYYC<u>ARRVSAITGGWAMDY</u>WGQGT
LVTVSS huVH8
SEQ ID NO: 12
EVRLMASGGGLVQPGGSLRLSCAASEFTFSNYAMSWVRQAPGKGLEWVATISRGGDYT
YYPDTVKGRFTISRDNSKNTLYLQMNSLRAEDTAVYYCARRVSMITGGYAMDYWGQGT
LVTVSS huVH9
SEQ ID NO: 13
EVRLMASGGGLVQPGGSLRLSCAASEFTFSNYAMSWVRQAPGKGLEWVATISRGGDYT
YYPDTVKGRFTISRDNSKNTLYLQMNSLRAEDTAVYYCARRVSMITGGFAMDYWGQGT
LVTVSS huVH10
SEQ ID NO: 14
EVRLMASGGGLVQPGGSLRLSCAASEFTFSNYAMSWVRQAPGKGLEWVATISRGGDYT
YYPDTVKGRFTISRDNSKNTLYLQMNSLRAEDTAVYYCARRVSMITGGAAMDYWGQGT
LVTVSS huVH11
SEQ ID NO: 15
EVRLMASGGGLVQPGGSLRLSCAASEFTFSNYAMSWVRQAPGKGLEWVATISRGGDYT
YYPDSVKGRFTISRDNSKNTLYLQMNSLRAEDTAVYYCARRVSMITGGWALDYWGQGT
LVTVSS huVH12
SEQ ID NO: 16
EVRLMASGGGLVQPGGSLRLSCAASEFTFSNYAMSWVRQAPGKGLEWVATISRGGDYT
YYPDSVKGRFTISRDNSKNTLYLQMNSLRAEDTAVYYCARRVSMITGGWAFDYWGQGT
LVTVSS huVH13
SEQ ID NO: 17
EVRLMASGGGLVQPGGSLRLSCAASEFTFSNYAMSWVRQAPGKGLEWVATISRGGDYT
YYPDSVKGRFTISRDNSKNTLYLQMNSLRAEDTAVYYCARRVSMITGGWAIDYWGQGT
LVTVSS huVH14
SEQ ID NO: 18
EVRLMASGGGLVQPGGSLRLSCAASEFTFSNYAMSWVRQAPGKGLEWVATISRGGDYT
YYPESVKGRFTISRDNSKNTLYLQMNSLRAEDTAVYYCARRVSMITGGWAMDYWGQGT
LVTVSS

LIST OF SEQUENCES huVH15
SEQ ID NO: 19
EVRLMASGGGLVQPGGSLRLSCAASEFTFSNYAMSWVRQAPGKGLEWVATISRGGDYT
YYPDTVKGRFTISRDNSKNTLYLQMNSLRAEDTAVYYCARRVSMITGGWAMDYWGQGT
LVTVSS huVH16
SEQ ID NO: 20
EVQLVESGGGLVQPGGSLRLSCAASEFTFSNYAMSWVRQAPGKGLEWVATISRGGDYT
YYPDSVKGRFTISRDNSKNTLYLQMNSLRAEDTAVYYCARRVSFITGGYAFDYWGQGT
LVTVSS huVH18
SEQ ID NO: 21
EVQLVESGGGLVQPGGSLRLSCAASEFTFSNYAMSWVRQAPGKGLEWVATISRGGDYT
YYPDSVKGRFTISRDNSKNTLYLQMNSLRAEDTAVYYCARRVSMITGGYAMDYWGQGT
LVTVSS huVH20
SEQ ID NO: 22
EVRLMASGGGLVQPGGSLRLSCAASEFTFSNYAMSWVRQAPGKGLEWVATISRGGDYT
YYPDSVKGRFTISRDNSKNTLYLQMNSLRAEDTAVYYCARRVSFITGGYAMDYWGQGT
LVTVSS huVH21
SEQ ID NO: 23
EVRLMASGGGLVQPGGSLRLSCAASEFTFSNYAMSWVRQAPGKGLEWVATISRGGDYT
YYPESVKGRFTISRDNSKNTLYLQMNSLRAEDTAVYYCARRVSFITGGYAMDYWGQGT
LVTVSS huVL1
SEQ ID NO: 24
DVVMTQSPLSLPVTLGQPASISCRSSQSIVDITGNTYLEWYQQRPGQSPRLLIYKVFN
RFSGVPDRFSGSGSGTDFTLKISRVEAEDVGVYYCFQDSFVPYTFGQGTKLEIK huVL2
SEQ ID NO: 25
DVVMTQSPLSLPVTLGQPASISCRSSQSIVDITGNTYLEWFQQRPGQSPRLLIYKVFN
RFSGVPDRFSGSGSGTDFTLKISRVEAEDVGVYYCFQDSFVPYTFGQGTKLEIK huVL3
SEQ ID NO: 26
DVVMTQSPLSLPVTLGQPASISCRSSQSIVDITGNTYLEWYQQRPGQSPRRLIYKVFN
RFSGVPDRFSGSGSGTDFTLKISRVEAEDVGVYYCFQDSFVPYTFGQGTKLEIK huVL4
SEQ ID NO: 27
DVVMTQSPLSLPVTLGQPASISCRSSQSIVDITGNTYLEWYQQRPGQSPRLLIYKVFN
RFSGVPDRFSGSGSGTDFTLKISRVEAEDVGVYYCFQESFVPYTFGQGTKLEIK huVL5
SEQ ID NO: 28
DVVMTQSPLSLPVTLGQPASISCRSSQSIVDITGNTYLEWYQQRPGQSPRLLIYKVFN
RFSGVPDRFSGSGSGTDFTLKISRVEAEDVGVYYCFQDTFVPYTFGQGTKLEIK huVL6
SEQ ID NO: 29
DVVMTQSPLSLPVTLGQPASISCRSSQSIVDITGNTYLEWFQQRPGQSPRRLIYKVFN
RFSGVPDRFSGSGSGTDFTLKISRVEAEDVGVYYCFQESFVPYTFGQGTKLEIK

IgG1m3 constant region of heavy chain
SEQ ID NO: 30
ASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFFLY
SKLTVDKSRWQQGNVFSCSVMHEALHNHYTQKSLSLSPGK IgKm3 constant region of light chain
SEQ ID NO: 31
RTVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

LIST OF SEQUENCES cVH1 (variable region of heavy chain from mouse B-E29)
SEQ ID NO: 32
EVRLMASGGGLVKPGGSLKLSCAASEFTFSNYAMSWVRQTPEKRLEWVATISRGGDYT
YYPDSVKGRFTISRDNAKNTLYLQMSSLRSEDTALYYCARRVSMITGGWAMDYWGQGT
SVTVSS cVH2
SEQ ID NO: 33
EVRLLASGGGLVKPGGSLKLSCAASEFTFSNYAMSWVRQTPEKRLEWVATISRGGDYT
YYPDSVKGRFTISRDNAKNTLYLQMSSLRSEDTALYYCARRVSMITGGWAMDYWGQGT
SVTVSS cVH3
SEQ ID NO: 34
EVQLLASGGGLVKPGGSLKLSCAASEFTFSNYAMSWVRQTPEKRLEWVATISRGGDYT
YYPDSVKGRFTISRDNAKNTLYLQMSSLRSEDTALYYCARRVSMITGGWAMDYWGQGT
SVTVSS cVH4
SEQ ID NO: 35
EVRLMESGGGLVKPGGSLKLSCAASEFTFSNYAMSWVRQTPEKRLEWVATISRGGDYT
YYPDSVKGRFTISRDNAKNTLYLQMSSLRSEDTALYYCARRVSMITGGWAMDYWGQGT
SVTVSS cVK1
SEQ ID NO: 36
DVLMTQTPLSLPVSLGDQASISCRSSQSIVDITGNTYLEWYLQKPGQSPKLLIYKVFN
RFSGVPDRFSGSGSGTDFTLKISRVEAEDLGLYYCFQDSFVPYTFGGGTKLEIK hVK2
SEQ ID NO: 37
EVVMTQSPATLSLSPGERATLSCRSSQSIVDITGNTYLEWYQQKPGQAPRLLIYKVFN
RFSGIPARFSGSGSGTDFTLTISSLEPEDFAVYYCFQDSFVPYTFGQGTKLEIK Human IL-2
SEQ ID NO: 38
MYRMQLLSCIALSLALVTNSAPTSSSTKKTQLQLEHLLLDLQMILNGINNYKNPKLTR
MLTFKFYMPKKATELKHLQCLEEELKPLEEVLNLAQSKNFHLRPRDLISNINVIVLEL
KGSETTFMCEYADETATIVEFLNRWITFCQSIISTLT VL-146B7
SEQ ID NO: 39
EIVLTQSPGTLSLSPGERATLSCRASQSVSSSYLAWYQQKPGQAPRLLIYGASRRATG
IPDRFSGSGSGTDFTLTISRLEPEDFAVYYCQRYGSSHTFGQGTKLEIS VH-146B7
SEQ ID NO: 40
EVQLVQSGAEVKKPGESLKISCKVSGYFFTTYWIGWVRQMPGKGLEYMGIIYPGDSDT
RYSPSFQGQVTISADKSISTAYLQWSSLKASDTAMYYCARGGNWNCFDYWGQGTLVTV
SS VL CDR3 DISC0280
Kabat positions: 89, 90, 91, 92, 93, 94, 95, 95A, 95B, 96, 97
SEQ ID NO: 41
AWYDRELSEWV VH CDR3 DISC0280
Kabat positions: 95, 96, 97, 98, 99, 100, 100a, 100b,
100c, 100d, 100e, 100f, 100g, 101, 102
SEQ ID NO: 42
DPAAWPLQQSLAWFDP IL-15 peptide fragment stretch
SEQ ID NO: 43
DTVENLIILANN

The invention claimed is:

1. An isolated antibody binding IL-15 comprising:
   a) a heavy chain variable region comprising SEQ ID NO: 5 or any variant thereof wherein 1, 2, 3, 4, 5 or 6 amino acids selected from arginine (R) at position H3 (VH RH3), methionine (M) at position H5 (VH MH5), alanine (A) at position H6 (VH AH6), alanine (A) at position H49 (VH AH49), aspartic acid (D) at position H61 (VH DH61), serine (S) at position H62 (VH SH62), methionine (M) at position H98 (VH MH98), tryptophan (W) at position H100C (VH WH100C), and methionine (M) at position H100E (VH MH100E) are substituted by a different amino acid, and
   b) a light chain variable region comprising SEQ ID NO: 24 or any variant thereof wherein 1, 2, 3, or 4 amino acids selected from tyrosine (Y) at position L36 (VL YL36), leucine (L) at position L46 (VL LL46), aspartic acid (D) at position L91 (VL DL91) and serine (S) at position L92 (VL SL92) are substituted by a different amino acid,
   or an antigen-binding fragment thereof.

2. The isolated antibody or antigen-binding fragment thereof according to claim 1, comprising:
   (1) a heavy chain variable region comprising SEQ ID NO: 5 or any variant thereof having at least 95% identity with SEQ ID NO: 5, and
   (2) a light chain variable region comprising SEQ ID NO: 24 or any variant thereof having at least 95% identity with SEQ ID NO: 24,
   or an antigen-binding fragment thereof.

3. The isolated antibody according to claim 1, which is a humanized antibody.

4. The isolated antibody or antigen-binding fragment thereof according to claim 1, wherein:

(1) said variant of SEQ ID NO: 5 has-comprising the amino acid sequence of SEQ ID NO: 5 except that:
  (i) VH RH3 is substituted by glutamine (Q), and/or VH MH5 is substituted by valine (V), and/or VH AH6 is substituted by glutamic acid (E), and/or VH AH49 is substituted by serine (S), and/or
  (ii) VH DH61 is substituted by glutamic acid (E), and/or VH SH62 is substituted by threonine (T), and/or
  (iii) VH MH98 is substituted by leucine (L), phenylalanine (F), isoleucine (1), or alanine (A), and/or VH WH100C is substituted by tyrosine (Y), phenylalanine (F), or alanine (A), and/or VH MH100E is substituted by leucine (L), phenylalanine (F), or isoleucine (I), and/or
(2) said variant of SEQ ID NO: 24 comprising the amino acid sequence of SEQ ID NO: 24 except that:
  (i) VL YL36 is substituted by phenylalanine (F), and/or VL LL46 is substituted by arginine (R), and/or
  (ii) VL DL91 is substituted by glutamic acid (E), and/or VL SL92 is substituted by threonine (T).

5. The isolated antibody or antigen-binding fragment thereof according to claim 1, comprising:
  (1) a heavy chain variable region comprising SEQ ID NO: 5 except that:
    (i) VH RH3 is substituted by glutamine (Q), and/or VH MH5 is substituted by valine (V), and/or VH AH6 is substituted by glutamic acid (E), and/or
    (ii) VH SH62 is substituted by threonine (T), and/or
    (iii) VH WH100C is substituted by tyrosine (Y), and
  (2) a light chain variable region comprising SEQ ID NO: 1.

6. The isolated antibody or antigen-binding fragment thereof according to claim 1, comprising:
  (1) a heavy chain variable region selected from: SEQ ID NO: 6, SEQ ID NO: 12, SEQ ID NO: 21, and SEQ ID NO: 5, and
  (2) a light chain variable region comprising SEQ ID NO: 24.

7. The isolated antibody or antigen-binding fragment thereof according to claim 1, comprising a heavy chain variable region of SEQ ID NO: 6 and a light chain variable region comprising SEQ ID NO: 24.

8. The isolated antibody or antigen-binding fragment thereof according to claim 1, which inhibits IL-15 activity.

9. A pharmaceutical composition comprising one or more of: (i) an antibody binding to IL-15 or antigen-binding fragment thereof according to claim 1 and at least one pharmaceutically acceptable carrier.

10. An ex vivo method for detecting the presence and/or concentration of IL-15 protein in a biological sample, comprising the steps of:
  (i) Providing a biological sample from a subject,
  (ii) Reacting said biological sample with at least one antibody or antigen-binding fragment thereof according to claim 1, under conditions sufficient for binding IL-15 protein present in said biological sample to said at least one antibody or fragment thereof through antigen-antibody interactions; and
  (iii) Detecting a signal proportional to the level of antigen-antibody complex formed in step (ii),
  wherein the intensity of the signal correlates with the concentration of IL-15 protein in the biological sample.

11. The isolated antibody according to claim 1, comprising:
  (1) a heavy chain variable region comprising a variant of SEQ ID NO: 5 wherein:
    (i) arginine (R) at position H3 (VH RH3), methionine (M) at position H5 (VH MH5), alanine (A) at position H6 (VH AH6) within the heavy chain variable framework region, or
    (ii) arginine (R) at position H3 (VH RH3), methionine (M) at position H5 (VH MH5), alanine (A) at position H6 (VH AH6), within the heavy chain variable framework region, and tryptophan (W) at position H100C (VH WH100C) within the heavy chain CDR3, or
    (iii) serine (S) at position H62 (VH SH62), within the heavy chain CDR2, and tryptophan (W) at position H100C (VH WH100C) within the heavy chain CDR3,
  are substituted by a different amino acid, and
  (2) a light chain variable region comprising SEQ ID NO: 24.

* * * * *

UNITED STATES PATENT AND TRADEMARK OFFICE
CERTIFICATE OF CORRECTION

PATENT NO. : 10,301,384 B2
APPLICATION NO. : 15/320763
DATED : May 28, 2019
INVENTOR(S) : Alain Vicari and Olivier Leger Page 1 of 1

It is certified that error appears in the above-identified patent and that said Letters Patent is hereby corrected as shown below:

In the Specification

Column 41,
Line 27, "CARRVSIITGGWAMDY" should read --CARRVSIITGGWAMDY--.
Line 31, "YYPDTVKGRFTISRDNSKNTLYLQMNSLRAEDTAVYYCARRVSAITGGWAMDYWGQGT" should read --YYPDTVKGRFTISRDNSKNTLYLQMNSLRAEDTAVYYCARRVSAITGGWAMDYWGQGT--.

In the Claims

Column 83,
Lines 31-32, "SEQ ID NO: 1" should read --SEQ ID NO: 24--.

Signed and Sealed this
Third Day of December, 2019

Andrei Iancu
*Director of the United States Patent and Trademark Office*